United States Patent
Munrow et al.

(10) Patent No.: US 9,861,336 B2
(45) Date of Patent: Jan. 9, 2018

(54) METHODS AND SYSTEMS FOR CONTROLLED DEPLOYMENT OF NEEDLE STRUCTURES IN TISSUE

(71) Applicant: Gynesonics, Inc., Redwood City, CA (US)

(72) Inventors: Michael A. Munrow, Belmont, CA (US); Darrin Uecker, San Mateo, CA (US); Brian Placek, Menlo Park, CA (US); Harry Kwan, San Francisco, CA (US); David Toub, Wyncote, PA (US); Cameron D. Hinman, Thurmond, NC (US); David J. Danitz, San Jose, CA (US)

(73) Assignee: Gynesonics, Inc., Redwood City, CA (US)

( * ) Notice: Subject to any disclaimer, the term of this patent is extended or adjusted under 35 U.S.C. 154(b) by 1057 days.

(21) Appl. No.: 13/801,782

(22) Filed: Mar. 13, 2013

(65) Prior Publication Data
US 2014/0073910 A1 Mar. 13, 2014

Related U.S. Application Data

(60) Provisional application No. 61/698,196, filed on Sep. 7, 2012.

(51) Int. Cl.
*A61B 8/08* (2006.01)
*A61B 18/14* (2006.01)
(Continued)

(52) U.S. Cl.
CPC ............ *A61B 8/0841* (2013.01); *A61B 5/066* (2013.01); *A61B 8/12* (2013.01); *A61B 8/445* (2013.01);
(Continued)

(58) Field of Classification Search
CPC ........................... A61B 90/36; A61B 18/1477
See application file for complete search history.

(56) References Cited

U.S. PATENT DOCUMENTS

| 5,469,853 A | 11/1995 | Law et al. |
| 6,050,992 A | 4/2000 | Nichols |

(Continued)

FOREIGN PATENT DOCUMENTS

| EP | 1649822 A1 | 4/2006 |
| JP | 2003534037 A | 11/2003 |

(Continued)

OTHER PUBLICATIONS

Office action dated Sep. 3, 2014 for U.S. Appl. No. 13/801,840.
(Continued)

*Primary Examiner* — Joseph M Santos Rodriguez
(74) *Attorney, Agent, or Firm* — Wilson, Sonsini, Goodrich & Rosati

(57) ABSTRACT

A system for deploying needles in tissue includes a controller and a visual display. A treatment probe has both a needle and tines deployable from the needle which may be advanced into the tissue. The treatment probe also has adjustable stops which control the deployed positions of both the needle and the tines. The adjustable stops are coupled to the controller so that the virtual treatment and safety boundaries resulting from the treatment can be presented on the visual display prior to actual deployment of the system.

19 Claims, 23 Drawing Sheets

(51) Int. Cl.

| | | |
|---|---|---|
| *A61N 7/00* | (2006.01) | |
| *A61M 5/46* | (2006.01) | |
| *A61B 8/00* | (2006.01) | |
| *A61B 5/06* | (2006.01) | |
| *A61B 8/12* | (2006.01) | |
| A61B 18/04 | (2006.01) | |
| A61B 18/18 | (2006.01) | |
| A61B 18/02 | (2006.01) | |
| A61B 18/00 | (2006.01) | |
| A61N 7/02 | (2006.01) | |
| A61B 34/10 | (2016.01) | |
| A61B 34/20 | (2016.01) | |
| A61B 90/00 | (2016.01) | |
| A61B 34/00 | (2016.01) | |
| A61B 17/32 | (2006.01) | |

(52) U.S. Cl.
CPC ............ *A61B 8/462* (2013.01); *A61B 8/463* (2013.01); *A61B 18/1477* (2013.01); *A61B 34/25* (2016.02); *A61M 5/46* (2013.01); *A61N 7/00* (2013.01); *A61B 8/461* (2013.01); *A61B 8/467* (2013.01); *A61B 18/02* (2013.01); *A61B 18/042* (2013.01); *A61B 18/1485* (2013.01); *A61B 18/1815* (2013.01); *A61B 90/04* (2016.02); *A61B 2017/320072* (2013.01); *A61B 2018/00559* (2013.01); *A61B 2018/00577* (2013.01); *A61B 2018/00702* (2013.01); *A61B 2018/00761* (2013.01); *A61B 2018/00898* (2013.01); *A61B 2018/00904* (2013.01); *A61B 2018/00982* (2013.01); *A61B 2018/0293* (2013.01); *A61B 2018/143* (2013.01); *A61B 2018/1475* (2013.01); *A61B 2034/104* (2016.02); *A61B 2034/107* (2016.02); *A61B 2034/2063* (2016.02); *A61B 2034/254* (2016.02); *A61B 2090/034* (2016.02); *A61B 2090/0427* (2016.02); *A61B 2090/378* (2016.02); *A61B 2090/3782* (2016.02); *A61B 2090/3784* (2016.02); *A61N 2007/025* (2013.01); *F04C 2270/041* (2013.01)

(56) References Cited

U.S. PATENT DOCUMENTS

| | | |
|---|---|---|
| 6,216,029 B1 | 4/2001 | Paltieli |
| 6,261,234 B1 | 7/2001 | Lin |
| 6,368,280 B1 | 4/2002 | Cermak et al. |
| 6,540,677 B1 | 4/2003 | Angelsen et al. |
| 6,585,694 B1 | 7/2003 | Smith et al. |
| 6,623,481 B1 | 9/2003 | Garbagnati et al. |
| 6,936,048 B2 | 8/2005 | Hurst |
| 6,944,490 B1 | 9/2005 | Chow |
| 6,969,354 B1 | 11/2005 | Marian |
| 7,160,296 B2 | 1/2007 | Pearson et al. |
| 7,229,401 B2 | 6/2007 | Kindlein |
| 7,387,628 B1 | 6/2008 | Behl et al. |
| 7,517,346 B2 | 4/2009 | Sloan et al. |
| 7,815,571 B2 | 10/2010 | Deckman et al. |
| 7,874,986 B2 | 1/2011 | Deckman et al. |
| 7,918,795 B2 | 4/2011 | Grossman |
| 7,963,941 B2 | 6/2011 | Wilk |
| 8,080,009 B2 | 12/2011 | Lee et al. |
| 8,088,072 B2 | 1/2012 | Munrow et al. |
| 8,157,741 B2 | 4/2012 | Hirota |
| 8,157,745 B2 | 4/2012 | Schoot |
| 8,206,300 B2 | 6/2012 | Deckman et al. |
| 8,216,231 B2 | 7/2012 | Behl et al. |
| 8,221,321 B2 | 7/2012 | McMorrow et al. |
| 8,262,574 B2 | 9/2012 | Placek et al. |
| 8,287,485 B2 | 10/2012 | Kimura et al. |
| 8,377,041 B2 | 2/2013 | Frassica et al. |
| 8,469,893 B2 | 6/2013 | Chiang et al. |
| 8,512,330 B2 | 8/2013 | Epstein et al. |
| 8,512,333 B2 | 8/2013 | Epstein et al. |
| 8,540,634 B2 | 9/2013 | Bruce et al. |
| 8,585,598 B2 | 11/2013 | Razzaque et al. |
| 8,622,911 B2 | 1/2014 | Hossack et al. |
| 8,663,130 B2 | 3/2014 | Neubach et al. |
| 8,718,339 B2 | 5/2014 | Tonomura et al. |
| 8,814,796 B2 | 8/2014 | Martin et al. |
| 9,089,287 B2 | 7/2015 | Sliwa et al. |
| 9,198,707 B2 | 12/2015 | McKay et al. |
| 9,198,719 B2 | 12/2015 | Murdeshwar et al. |
| 9,247,925 B2 | 2/2016 | Havel et al. |
| 9,439,627 B2 | 9/2016 | Case et al. |
| 9,510,898 B2 | 12/2016 | Epstein et al. |
| 9,516,996 B2 | 12/2016 | Diolaiti et al. |
| 2003/0195502 A1 | 10/2003 | Garabedian et al. |
| 2006/0189972 A1 | 8/2006 | Grossman |
| 2006/0276811 A1 | 12/2006 | Copa et al. |
| 2007/0006215 A1 | 1/2007 | Epstein et al. |
| 2007/0016183 A1 | 1/2007 | Lee et al. |
| 2007/0179380 A1 | 8/2007 | Grossman |
| 2007/0249939 A1 | 10/2007 | Gerbi et al. |
| 2008/0033493 A1 | 2/2008 | Deckman et al. |
| 2008/0228081 A1 | 9/2008 | Becker et al. |
| 2009/0043295 A1 | 2/2009 | Arnal et al. |
| 2009/0099544 A1 | 4/2009 | Munrow et al. |
| 2009/0171218 A1 | 7/2009 | Nygaard et al. |
| 2010/0056926 A1 | 3/2010 | Deckman et al. |
| 2010/0262133 A1 | 10/2010 | Hoey et al. |
| 2011/0218444 A1 | 9/2011 | Steffen |
| 2011/0288540 A1 | 11/2011 | Wright et al. |
| 2012/0035474 A1 | 2/2012 | Deckman et al. |
| 2012/0165813 A1 | 6/2012 | Lee et al. |
| 2012/0209115 A1 | 8/2012 | Tonomura |
| 2012/0277737 A1 | 11/2012 | Curley |
| 2013/0281863 A1 | 10/2013 | Chiang et al. |
| 2013/0317366 A1 | 11/2013 | Hirayama et al. |
| 2014/0180273 A1 | 6/2014 | Nair |
| 2014/0276081 A1 | 9/2014 | Tegels |
| 2015/0150497 A1 | 6/2015 | Goldchmit |
| 2015/0173592 A1 | 6/2015 | Leeflang et al. |
| 2015/0257779 A1 | 9/2015 | Sinelnikov et al. |
| 2016/0151041 A1 | 6/2016 | Lee et al. |
| 2016/0278740 A1 | 9/2016 | Negrila et al. |
| 2016/0310042 A1 | 10/2016 | Kesten et al. |

FOREIGN PATENT DOCUMENTS

| | | |
|---|---|---|
| JP | 2009526554 A | 7/2009 |
| JP | 2011500164 A | 1/2011 |
| JP | 2012519037 A | 8/2012 |
| WO | WO-2007149595 A2 | 12/2007 |
| WO | WO 2009/049082 A1 | 4/2009 |
| WO | WO 2010/027820 A1 | 3/2010 |
| WO | WO-2010099481 A1 | 9/2010 |

OTHER PUBLICATIONS

Notice of allowance dated Jan. 7, 2015 for U.S. Appl. No. 13/801,840.
International search report and written opinion dated Dec. 11, 2013 for PCT/US2013/058467.
U.S. Appl. No. 13/801,840, filed Mar. 13, 2013, Munrow et al.

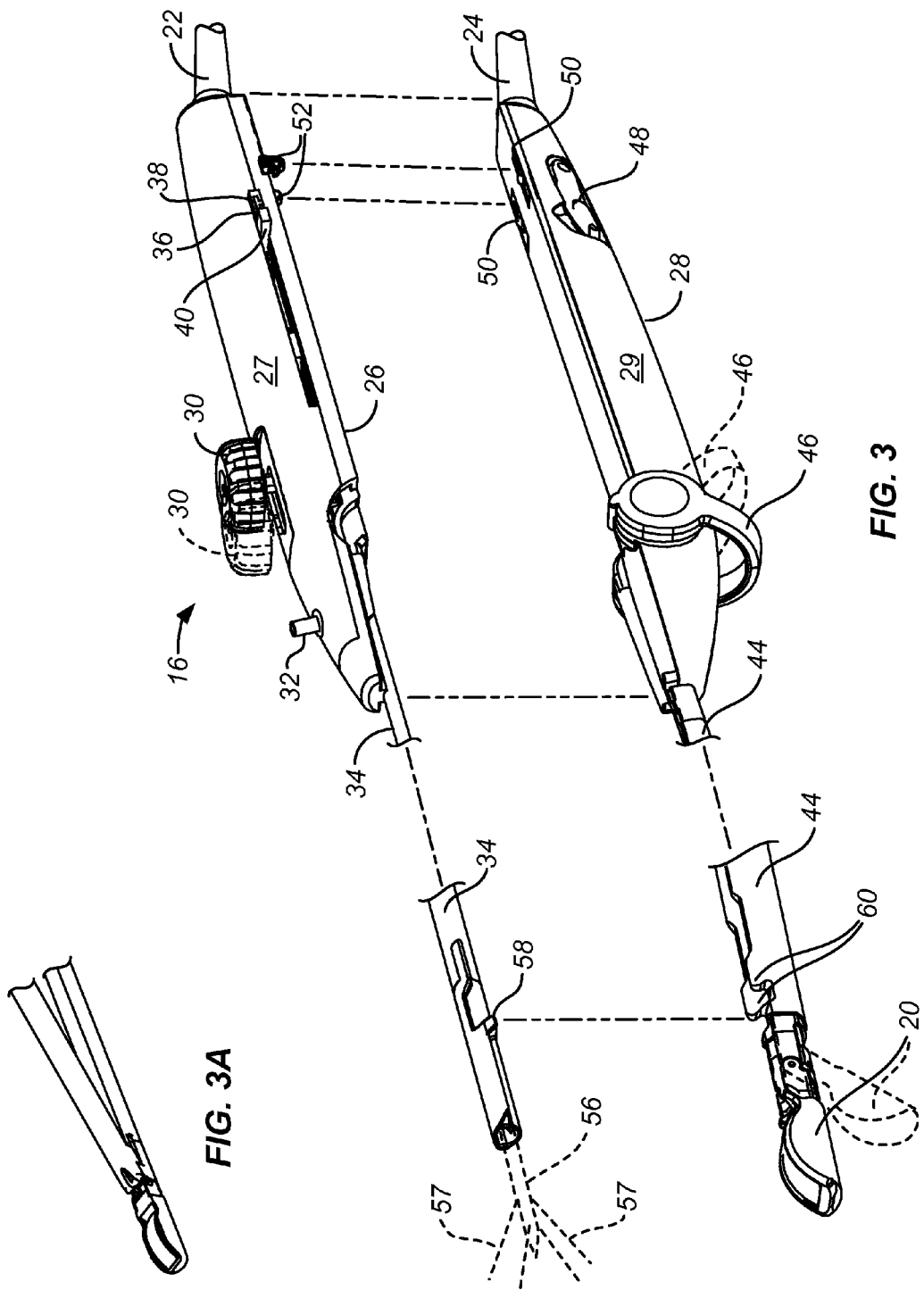

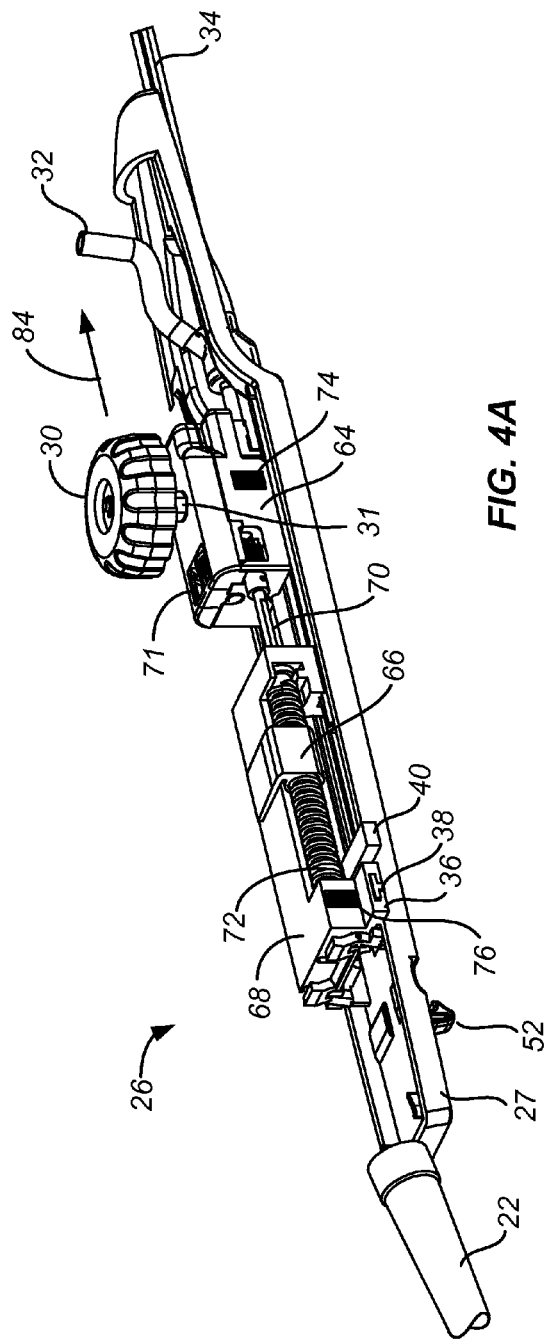
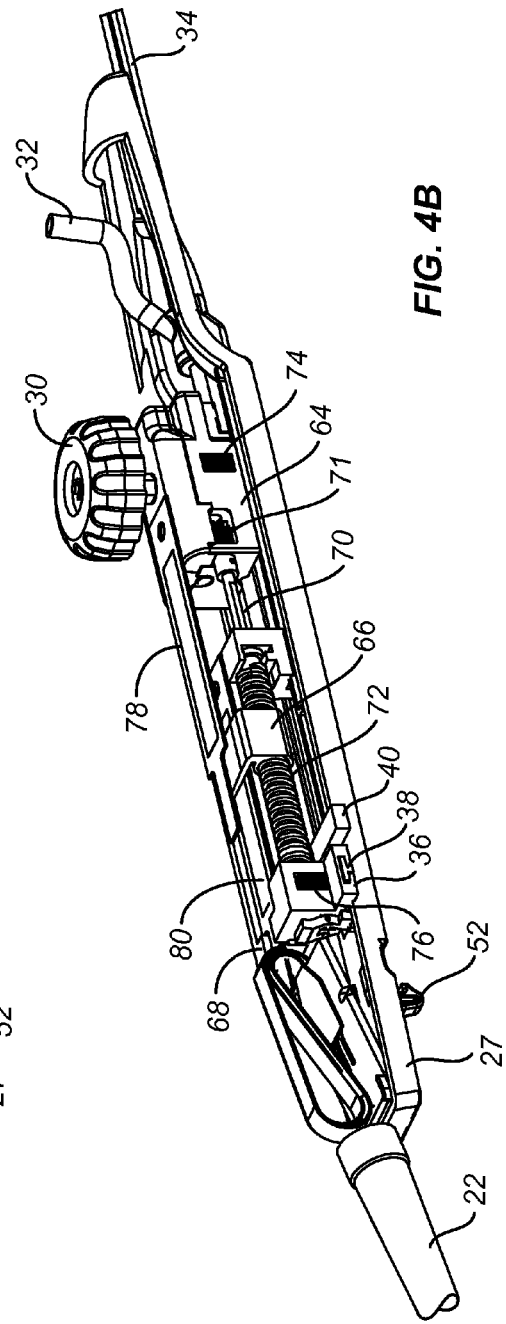
FIG. 4A
FIG. 4B

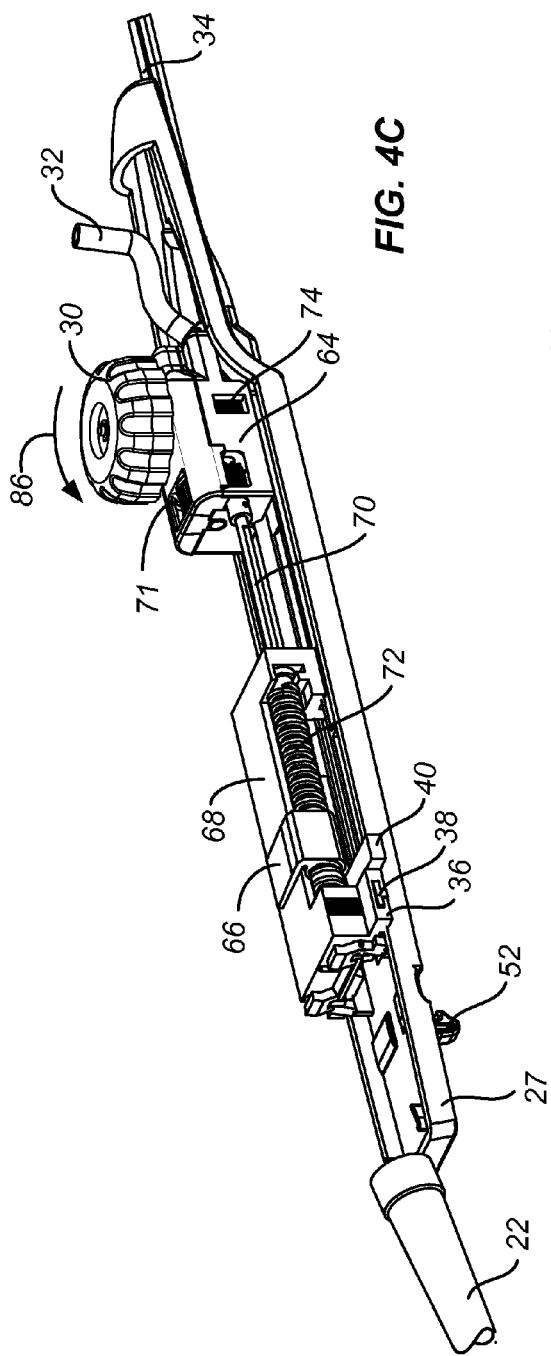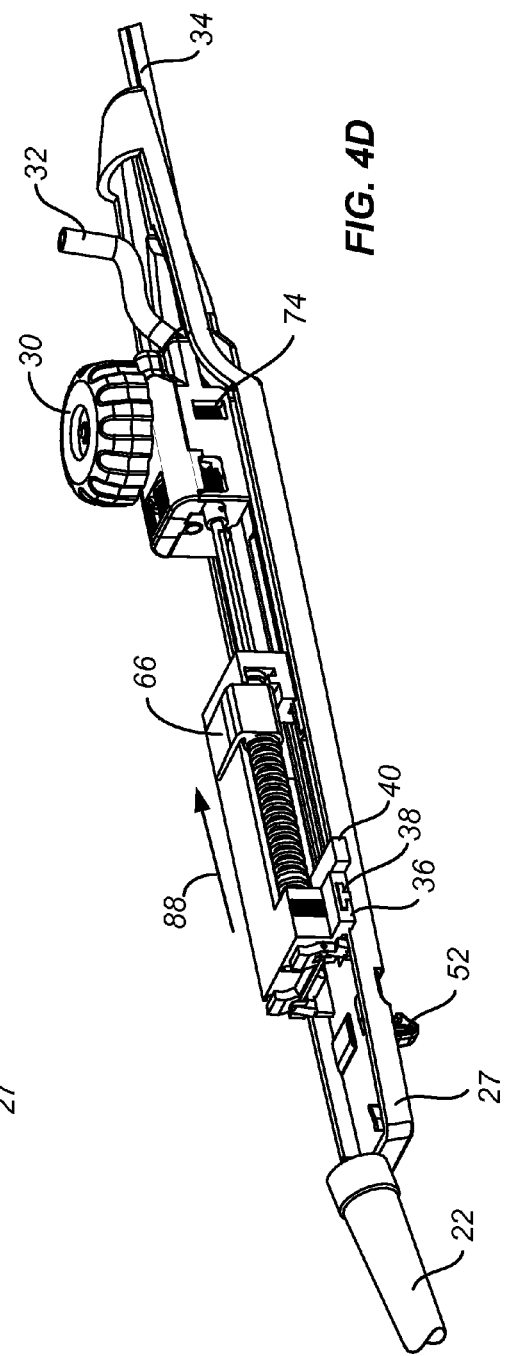

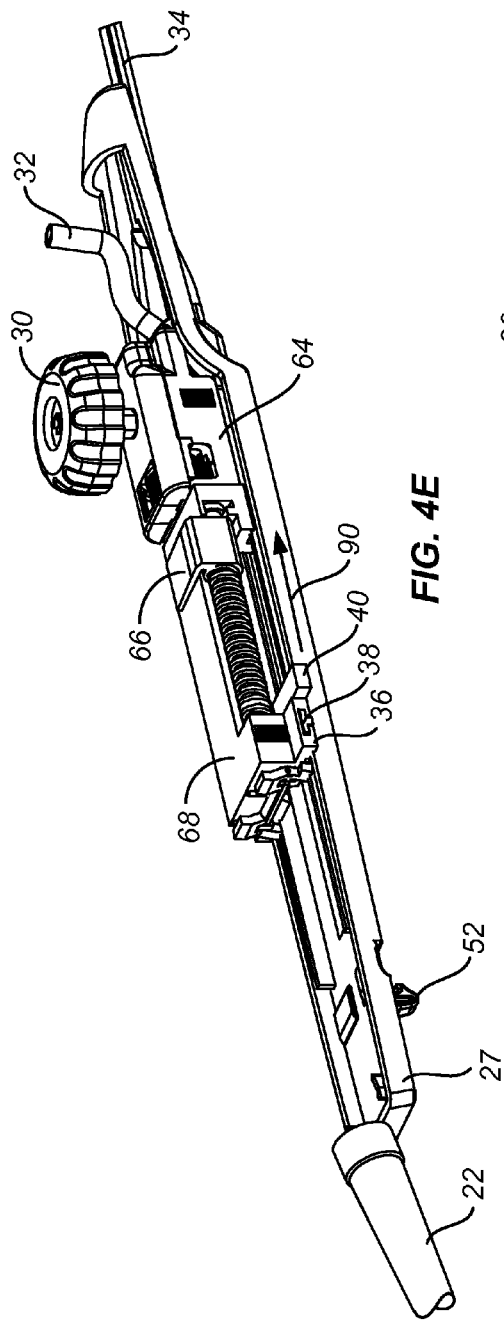
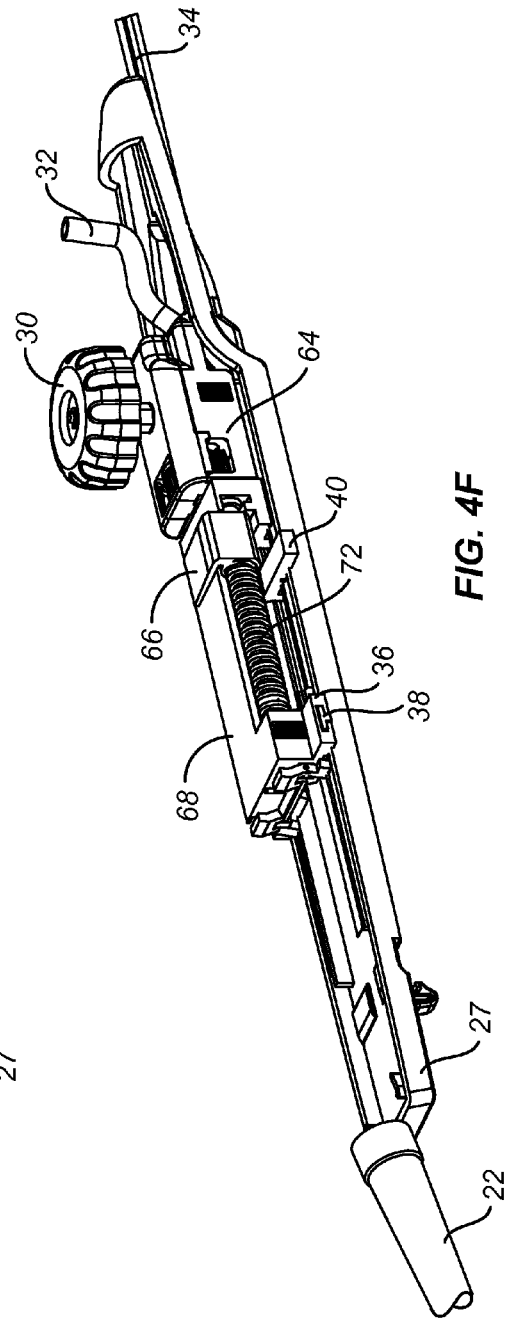

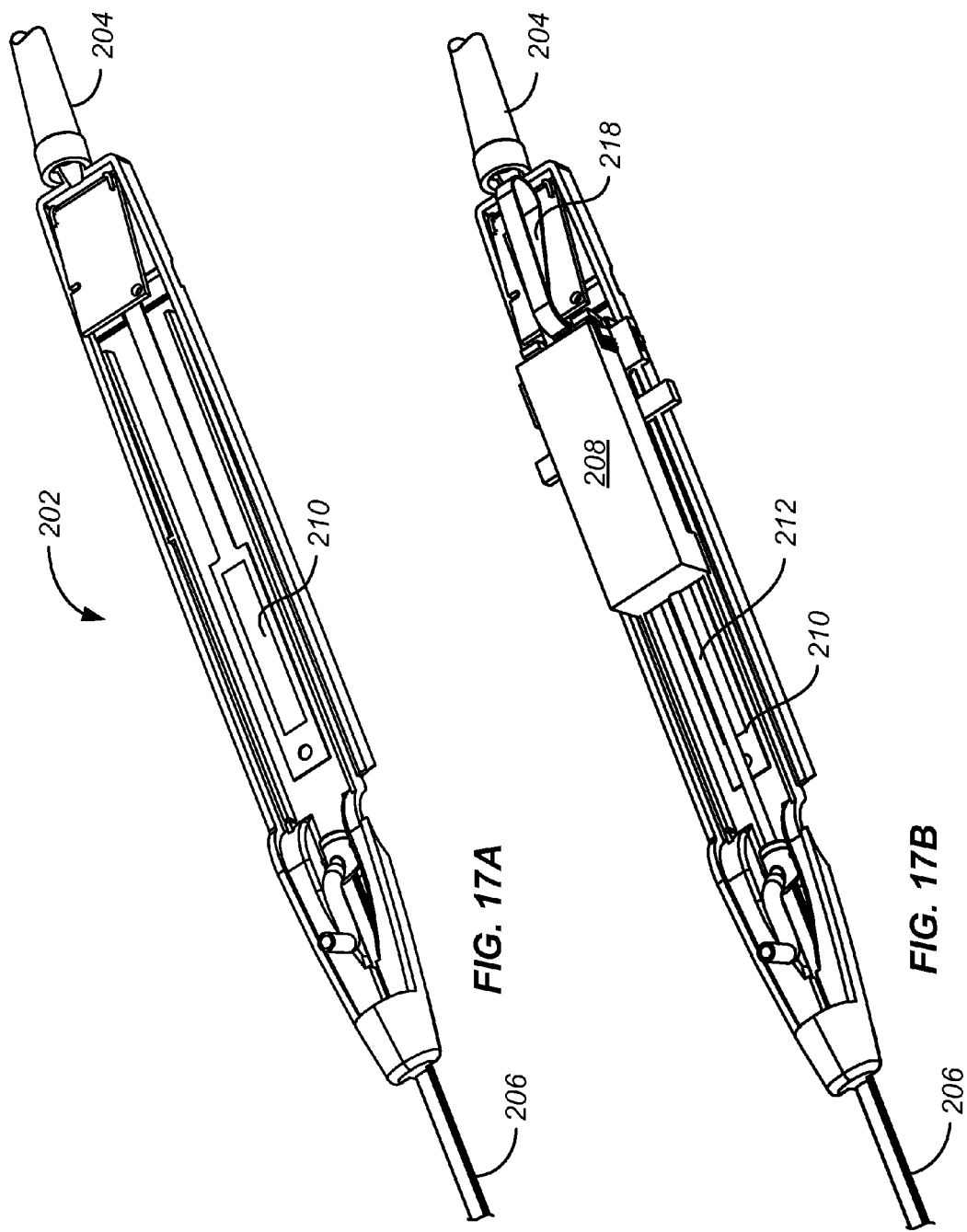

METHODS AND SYSTEMS FOR CONTROLLED DEPLOYMENT OF NEEDLE STRUCTURES IN TISSUE

CROSS-REFERENCE TO RELATED APPLICATIONS

This application claims the benefit of Provisional Application No. 61/698,196, filed Sep. 7, 2012, the full disclosure of which is incorporated herein by reference.

BACKGROUND OF THE INVENTION

1. Field of the Invention

The present invention relates generally to medical methods and apparatus. More particularly, the present invention relates to methods and systems for controlling the deployment of needles using treatment and safety boundaries projected onto an image of tissue to be treated.

Current medical treatments of organs and tissues within a patient's body often use a needle or other elongate body for delivery of energy, therapeutic agents or the like. Optionally the methods use ultrasound imaging to observe and identify a treatment target and track the position of the needle relative to the treatment target.

Of particular interest to the present invention, a treatment for uterine fibroids has recently been proposed which relies on the transvaginal or laparoscopic positioning of a treatment device in the patient's uterus. A radiofrequency or other energy or therapeutic delivery needle is deployed from the device into the fibroid, and energy and/or therapeutic substances are delivered in order to ablate or treat the fibroid. To facilitate locating the fibroids and positioning the needles within the fibroids, the device includes an ultrasonic imaging array with an adjustable field of view in a generally forward or lateral direction relative to an axial shaft which carries the needle. The needle is advanced from the shaft and across the field of view so that the needle can be visualized and directed into the tissue and the targeted fibroid.

While effective and very beneficial for patients, such needle ablation and treatment protocols face several challenges. First, initial deployment of the needle can be difficult, particularly for physicians who have less experience. While the physician can view the tissue and target anatomy in real time on an imaging screen, it can be difficult to precisely predict the path the needle will take and assess its final treatment position. While the needle can certainly be partially or fully retracted and redeployed, it would be advantageous to minimize the number of deployments required before treatment is effected.

A second challenge comes after the needle has been deployed. While the position of the needle can be observed on the ultrasonic or other visual image, the treatment volume resulting from energy or other therapeutic delivery can be difficult to predict. As with initial positioning, experience will help but it would be desirable to reduce the need to exercise judgment and conjecture.

A third challenge lies in assuring that nearby sensitive tissue structures, such as the serosa surrounding the myometrium, are not unintentionally damaged. As with judging the treatment volume, predicting the safety margin of the treatment can be difficult.

U.S. Pat. No. 8,088,072, commonly assigned with the present application, describes a system for projecting safety and treatment boundaries on a real time image of the fibroid or other tissue structure to be treated. While very effective when used with single needles, the system of the '072 patent is not optimized for use with multiple needle/tine assemblies, such as those taught in commonly owned U.S. Pat. Nos. 8,206,300 and 8,262,574.

For these reasons, it would be desirable to provide improved systems and methods for the deployment of energy delivery and other needles within ultrasonic or other imaging fields of view in energy delivery or other therapeutic protocols. It would be particularly useful to provide the treating physician with information which would assist in initial deployment of a plurality of needles or tines in order to improve the likelihood that the needle assembly will be properly positioned relative to a targeted anatomy to be treated. It would also be desirable to provide feedback to the physician to assist in accurately predicting a treatment volume. Such information should allow the physician, if necessary, to reposition the probe in order to increase the likelihood of fully treating the anatomy. Furthermore, it would be desirable to provide feedback to the physician allowing the physician to assess a safety margin so that sensitive tissue structures are not damaged. All such feedback or other information are preferably provided visually on the ultrasonic or other imaging screen so that the needle position can be quickly predicted, assessed, and treatment initiated. It would be further desirable if the feedback information were presented on a display screen in response to manipulating the probe while minimizing the need to enter data or commands onto a system controller or display, and still further desirable if such manipulation of the probe could set stops or other limits which controlled the extent of subsequent needle deployment. At least some of these objectives will be met by the inventions described hereinafter.

2. Description of the Background Art

U.S. Pat. Nos. 8,088,072; 8,206,300 and 8,262,574 have been described above and are incorporated herein by reference. U.S. Pat. No. 7,918,795, commonly assigned with the present application, describes probes useful for both imaging and treating uterine fibroids, which probes could be used in the systems and methods of the present application and is incorporated herein by reference. Other commonly assigned patents and published applications describing probes useful for treating uterine fibroids in the systems include U.S. Pat. Nos. 7,874,986 and 7,815,571; and U.S. Patent Publications 2007/0179380 and 2008/0033493. See also U.S. Pat. No. 6,050,992 and U.S. patent Publication 2007/0006215.

BRIEF SUMMARY OF THE INVENTION

The present invention provides methods and systems for deploying needle structures in tissue. The needle structures may in some cases comprise a single needle but in most cases will comprise multiple needles or needle and tine assemblies as described in more detail below. The needle structures are usually intended to deliver a therapy to the tissue, most typically being configured to deliver radiofrequency energy, plasma energy, therapeutic ultrasound energy, microwave energy, heat, cold (cryogenic treatment), or other energy to ablate or otherwise modify a target tissue or targeted anatomy within the tissue. Alternatively, the needle structures could also provide drug or other substance delivery, morcellation, or other tissue treatments which can be effected using a needle structure.

The methods and systems of the present invention are particularly suitable for treating fibroids in a patient's uterus where a probe carrying the needle structure and an imaging transducer, typically an ultrasonic imaging transducer, is introduced transvaginally and transcervically into the uterus, or in other cases laparoscopically into and through an exterior of the uterus or other organ or tissue target. The probe is manipulated within the uterus to deliver ablative energy to the fibroid as described in more detail below. In most embodiments of the present invention, the needle structure is "virtually" deployed on a real-time image of the tissue prior to actual deployment of the needle in the actual tissue. Treatment and/or safety boundaries within the tissue will also be determined and optionally adjusted prior to the actual deployment of the needle structure. In other embodiments, the actual position of the needle structure may be tracked and the corresponding treatment and/or safety boundaries projected on the screen in real time. In all embodiments, the treatment and safety boundaries can be checked before treatment is commenced.

The methods and systems of the present invention further provide that, once the parameters of the virtual deployment have been selected using the virtual images, the needle structure is actually deployed in the real tissue at a location and/or in a pattern which matches the virtual deployment configuration. In a first exemplary embodiment, such deployment is achieved by manipulating "stops" or other mechanical elements on the probe during the virtual deployment on the real-time image. The stop positions correspond to actual needle deployment positions (the stops typically act as limits which allow the needle structure to be deployed to a specific location and in a specific pattern), and the system calculates the treatment and/or safety boundaries based on the stop positions as well as on energy delivery data which is supplied to or generated by a system controller. This system may alternatively or additionally track the position of the treatment probe and/or needle structure in the uterus, thus allowing the treatment and safety boundaries which are projected upon the real-time image of the tissue to be calculated and/or updated as the probe is moved and the needle structure advanced by the treating physician. In the first exemplary embodiment, once the treatment region and/or safety boundary are properly positioned on the real-time image relative to the anatomy to be treated, the physician may hold the probe in place and deploy the needle structure until it reaches its "stop" position(s) which have been preset into the probe during the initial imaging and set-up phase of the treatment. In some cases, the stops can be automatically set as the physician manipulates the treatment and/or safety boundary on the screen using the controls on the treatment probe. In alternative embodiments, the physician may manipulate the probe and advance the needle structure while viewing the safety and/or treatment boundaries in real time without having previewed the virtual projections.

In the exemplary embodiments, at least one main or central needle will be deployed from the treatment probe, and a plurality of tines or secondary needles will be deployed from the main or central needle(s). Most often, there will be a single main needle which is deployed distally from a shaft of the probe along a central axis thereof. A plurality of tines will then be advanced from the single needle in a distally diverging pattern. In other embodiments, a plurality of needles or tines may be advanced from the probe without use of a main or central needle. In such cases, the needles or tines will typically expand or diverge into a three-dimensional array as they are advanced distally.

Exemplary anatomical features that may be imaged and subsequently treated include fibroids, tumors, encapsulated tissue masses, pseudoencapsulated tissue masses, and the like. Of particular interest of the present invention, the probe may be positioned in the uterus and the needle structure deployed to a location proximate to or within a fibroid located in the myometrium tissue of the uterus. In such cases, it will be desirable to also image the serosa which surrounds the myometrium and/or other sensitive anatomical features that could be damaged by the energy-mediated treatments described herein.

As used herein, a treatment region is defined by a treatment boundary which is calculated by the system controller based upon the needle structure deployment configuration (either as set by the "stops" or as calculated in real-time as the needle structure is deployed) and the energy delivery parameters set by or input into the system controller. Energy or other therapy delivered by the needle structure deployed in the selected pattern at the selected location will effectively treat the target tissue to achieve ablation or other therapeutic results. As described below, it will thus be desirable to manipulate the probe as well as the needle structure stop(s) and/or actual needle structure so that the treatment region at least partially surrounds the anatomy to be treated as seen on the real-time image display of the system.

As further used herein, the safety region is defined by a safety boundary which is calculated by the system. As with the treatment region, the safety boundary is calculated based upon the needle structure "stops" and/or actual needle structure positions which have been set or adjusted on the treatment probe by the physician as well as the energy delivery parameters which are input into or set by the system controller. The safety boundary will differ from the treatment boundary in that the safety boundary will be set at a minimum threshold distance beyond the boundary of the tissue treatment region where the risk of damaging tissue is reduced or eliminated entirely.

In a first aspect of the present invention, methods for deploying a needle structure in tissue comprise positioning a treatment probe having a deployable needle structure near a surface of the tissue to be treated, for example, adjacent to a uterine wall over the myometrium of a uterus. A real-time image of the tissue is provided, typically using an imaging transducer such as an ultrasonic array which is carried by the treatment probe, and projected onto a display connected to a controller. The real-time image includes an anatomical feature to be treated, such as a fibroid. At least one of a treatment region and a safety region is projected onto the real-time image prior to deploying the needle structure. A size and/or a position of a boundary of the treatment region and/or the safety region is then adjusted on the real-time image still prior to deploying the needle structure. After the boundary(ies) of the treatment region and/or the safety region are properly positioned on the real-time image relative to the anatomy to be treated, the needle structure may be deployed from the probe into the tissue to provide treatment within the projected treatment/safety boundary after the boundary has been adjusted.

The boundary of the treatment region and/or safety region can be moved or adjusted in several ways. First, manual movement of the probe by the physician will cause the real time image of the tissue and anatomy projected on the screen to move relative to the treatment/safety boundary(ies) projected on the screen. Since the position(s) of the treatment and/or safety boundary projected on the screen depends on the calculated position of the needle structure, it will be appreciated that movement of the probe itself will cause the calculated needle position to move within the real-time image. In addition to such gross movement of the treatment probe in the uterus, the position of the treatment or safety region projected on the real-time image can be adjusted by controls on the probe, e.g. by manually positioning a needle stop element provided on the probe. The needle stop element provides a physical limit on deploying at least one needle of the needle structure so that when the needle is actually deployed in tissue, the needle will be precisely located at the position determined by the needle stop. Prior to deployment, the position of the needle stop itself is tracked by the system controller and used to calculate the position(s) of the treatment and/or safety boundaries.

In specific embodiments, one or more sensor(s) on the probe track(s) movement of the stop(s) in order to reposition and/or resize the projected boundaries. For example, a rotary sensor could be provided on the targeting knob so that when the knob is rotated, the treatment region grows and shrinks and a gear train turns a lead screw which moves the stop. Thus, sensors coupled to the stops track the projected safety/treatment boundary.

Alternatively, in other embodiments, the position(s) and size(s) of the treatment and/or safety boundaries may be adjusted on the controller and/or display screen using an appropriate interface, such as a keyboard, joy stick, mouse, touch panel, touch screen, or the like. Once the treatment and/or safety boundaries are properly (virtually) positioned on the screen, the controller can control the deployment of the needle structure on the treatment probe. For example, the controller could position servo motors on the probe to position the needle/tine stops or could directly position the needles/tines without the use of stop structures.

In addition to the needle stop, the probe will usually also have a tine stop which determines the extent to which a plurality of tines may be advanced from the needle. While the present disclosure generally refers to a single tine stop, other embodiments may employ multiple tine stops, and the individual tines may be individually controlled or be controlled in groups of less than the whole. The tine stop will be configured to be monitored by the system controller so that the controller can calculate the size of the treatment or safety boundary as the tine stop is adjusted. Additionally, once the desired position and size of the treatment and/or safety boundaries are determined, the tine stop will act to limit the travel of the tines so that they are physically deployed in a pattern which provides treatment within the desired treatment/safety boundaries when energy is delivered through the needle structure.

Once the needle stop and tine stop have been set, and the needle structure has been advanced in tissue to the limits defined by the stops, energy may be delivered through the needle structure to treat the tissue. The energy, of course, will be delivered at a treatment power and/or treatment time which has been used to calculate the treatment region and/or safety region boundaries. In some embodiments, it will be possible for the controller to adjust the position or size of the treatment or safety boundaries based on the power, time and/or other treatment parameters (in addition to needle/tine position) which have been selected by the physician. In this way, both the needle/tine positions and the power and time of energy delivery are taken into account to calculate the position or size of the treatment or safety boundaries. Alternatively, drug delivery, tissue morcellation, and other therapies could be delivered through the deployed needle structure.

Optionally, virtual needle location information can be projected onto the real-time image while the position and/or size of the treatment and/or safety boundaries are being adjusted. For example, the needle location information could comprise a plurality of fiducials or markers which are projected onto the real-time image to indicate the projected positions of the needle tip(s), or other needle position information. In other cases, it would be possible to project complete images of the needle lengths as they would travel through the tissue (but prior to actual deployment). The needle location information would, of course, preferably be updated as the probe stops are being adjusted and would allow the physician to see where the needle will be after needle deployment.

In another aspect of the present invention, a system for treating an anatomical feature in tissue comprises a real-time image display, a treatment probe, and a positionable stop structure on the treatment probe. The treatment probe carries a deployable needle structure and an imaging transducer, wherein the transducer is connectable to the real-time image display. The position stop structure on the probe (1) controls at least one of a position or size of a treatment or safety region projected on the real-time image display and (2) physically limits deployment of the needle structure so that subsequent treatment of the tissue is within the treatment and/or safety region.

An exemplary needle structure comprises a needle and a plurality of tines which may be advanced from the needle. The tines assume a distally diverging pattern as they are advanced from the needle, and the stop structure typically comprises a needle stop element and a separate tine stop element. The needle stop element at least partially controls the position of the treatment or safety region projected on the real-time image display and the tine stop element at least partially controls the size of the treatment or safety region projected on the real-time image display.

The treatment systems may optionally further comprise a controller connectable to the probe for delivering energy to the needle structure, where the system is configured to control the projected treatment size or projected safety region size based upon both an energy level to be delivered by the controller and the position of the stop element(s) which may be tracked by sensors on the treatment probe In a further aspect of the present invention, an imaging and therapeutic delivery system comprises an imaging component comprising an imaging shaft having a proximal end, a distal end, and an imaging transducer at the distal end. A needle component comprising a needle shaft having a distal end and a proximal end and a needle structure reciprocally disposed on or within the shaft is configured to removably attach to the imaging shaft with the shafts lying side-by-side with their respective axes in parallel.

In specific examples, the imaging transducer on the imaging shaft is pivotally attached at the distal end of the imaging shaft, and the distal end of the needle shaft is disposed proximally of the pivotally attached imaging transducer when the needle shaft is attached to the imaging shaft. The needle structure in the needle shaft typically reciprocates distally along the axis of the needle shaft, and the imaging transducer pivots away from the axis of the needle shaft when the needle shaft is attached to the imaging shaft. The imaging component may further comprise an imaging handle section attached to a proximal end of the imaging shaft, and the needle component may further comprise a needle handle section attached to a proximal end of the needle shaft. In such embodiments, the imaging handle section and needle handle section will typically form a complete handle when the needle shaft is attached to the imaging shaft. The imaging handle section usually has an interior which holds circuitry configured to connect the imaging transducer with an external imaging display and the needle handle section including mechanisms for advancing the tine needle structure, and the imaging handle section usually further comprises mechanisms for pivoting the imaging transducer relative to the imaging shaft.

In a still further aspect of the present invention, a method for deploying a plurality of tines from a needle in tissue comprises providing a real-time image of the tissue, including an anatomical feature to be treated, on a display. The needle is penetrated into tissue proximate the anatomical feature, typically in a distal direction, and tines are deployed from the needle further into the tissue. As with previous embodiments, the tines typically diverge radially as they are advanced distally from the needle to increase the volume of tissue to be treated. At least one of a treatment boundary and a safety boundary are projected onto the display in response to the tine deployment. An extent of the tine deployment can be adjusted to change the size and/or shape of the treatment and/or safety boundary which is projected on the display. In contrast to prior embodiments, the physician is able to position the needle and tines without having previously virtually projected the safety and/or treatment boundaries onto the image of the anatomy. Instead, the actual needle and tine deployment can be relied on to position and reposition the safety and/or treatment boundaries on the real time image until the physician is satisfied that a subsequent treatment will be both safe and effective using the actually deployed needle and tine configuration. In addition to the actual needle and tine deployment, of course, the projected treatment and/or safety boundaries will also depend on the intended power and time lengths of the treatment in a manner analogous to the projections of the virtual boundaries discussed previously. After an acceptable size and/or safety boundary has been achieved, the treatment may be delivered through the tines. In particular embodiments, deployment of the tines may be tracked via sensors in a needle/tine deployment mechanism on a probe used to deploy the needle and tines. In such cases, penetrating the needle will comprise advancing the needle from the probe which has been penetrated into the tissue. Usually, the extent of needle deployment from the probe will also be relied on in determining the projected safety and/or treatment boundaries on the display.

In still further aspects of the present invention, a system for treating an anatomical feature in tissue comprises a real-time display connected to a controller. The system projects and adjusts a size of at least one of a treatment boundary and a safety boundary onto the display. A treatment probe having a deployable needle structure and an imaging transducer is provided which is connectable to the controller and the display. The treatment probe carries at least one servo drive motor which is connected to and driven by the controller. The controller is configured to drive the servo motor to position the needle structure to provide a treatment which is effective over the region defined by the treatment boundary and which does not extend significantly beyond the safety boundary.

In specific embodiments of the system, the needle structure may comprise a needle and a plurality of tines advanceable from the needle in a distally diverging pattern. The at least one servo motor may comprise a first servo motor which drives the needle and a second servo motor which drives the plurality of tines. The system usually comprises a user interface configured to allow the user to virtually adjust the size and/or a position of the treatment and/or safety boundary on the display. In some instances, as described previously, an interface may be on the treatment probe itself. In other cases, the interface may comprise a more conventional keyboard, mouse, roller ball, touch screen, voice activation, or the like which is connected to the controller to allow the user to virtually position the needle structure prior to actually positioning the needle structure. In still other embodiments, the treatment probe may comprise servo motors for positioning the needle structure and/or sensors for detecting the extent to which the needle structure has been deployed. In such cases, the user may position the needle structure using the servos (without having generated a virtual projection of the safety and/or treatment boundaries), and observe the projected safety and/or treatment boundaries as they are calculated and projected by the system controller. In all cases, the system can be used to deliver energy or other treatments only after the deployment of the needle structure has been confirmed to meet the requirements of the safety and/or treatment boundaries.

All publications, patents, and patent applications mentioned in this specification are herein incorporated by reference to the same extent as if each individual publication, patent, or patent application was specifically and individually indicated to be incorporated by reference.

BRIEF DESCRIPTION OF THE DRAWINGS

FIG. 3 is a view of the treatment probe of FIG. 2 illustrating an imaging component of the probe separated from a needle component with portions broken away and portions enlarged.

FIG. 3A illustrates a distal end of the needle component being connected to a distal end of the imaging component.

FIGS. 4A through 4F illustrate the internal mechanisms of the needle deployment component of the probe, including a needle stop housing and a needle carriage, showing how the mechanisms are manipulated in order to deploy the needle structure.

FIGS. 10A-15A illustrate "screenshots" of the real-time image display as the treatment and safety boundaries are being adjusted using the treatment probe in accordance with the principles of the present invention.

FIGS. 10B-15B illustrate manipulation of the handle which corresponds to the repositioning of the projected images of the treatment and safety boundaries on the real-time images of FIGS. 10A-15A.

FIG. 17A-17C illustrate an alternative construction of the needle housing of the present invention having sensors for detecting the positions of the needle carriage and the tine slide as they are positioned to deploy the needle and tines, respectively.

DETAILED DESCRIPTION OF THE INVENTION

Figure 1:
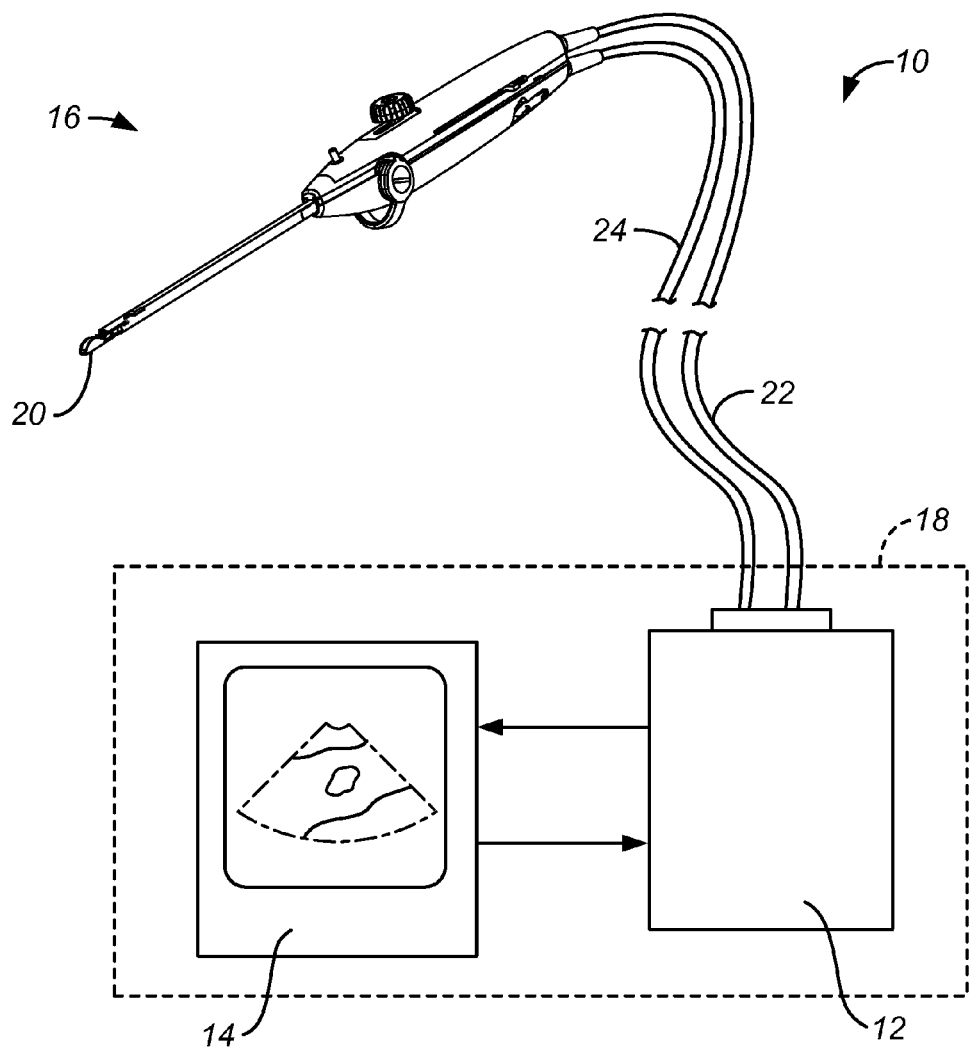
FIG. 1 is a schematic illustration of the system of the present invention comprising a system controller, an image display, and a treatment probe having a deployable needle structure and imaging transducer.

As illustrated in FIG. 1, a system 10 constructed in accordance with the principles of the present invention includes a system controller 12, an imaging display 14, and a treatment probe 16. The system controller 12 will typically be a microprocessor-based controller which allows both treatment parameters and imaging parameters to be set in a conventional manner. The display 14 will usually be included in a common enclosure 18 together with the controller 12, but could be provided in a separate enclosure. The treatment probe 16 includes an imaging transducer 20 which is connected to the controller 12 by an imaging cord 24. The controller 12 supplies power to the treatment probe via a treatment cord 22. The controller 12 will typically further include an interface for the treating physician to input information to the controller, such as a keyboard, touch screen, control panel or the like. Optionally, a touch panel may be part of the imaging display 14. The energy delivered to the treatment probe by the controller may be radiofrequency (RF) energy, microwave energy, a treatment plasma, heat, cold (cryogenic therapy), or any other conventional energy-mediated treatment modality. Alternatively or additionally, the treatment probe could be adapted to deliver drugs or other therapeutic agents to the tissue anatomy to be treated. In some embodiments, probe 16 plugs into an ultrasound system and into a separate radio frequency (RF) generator. An interface line connects the ultrasound system and the RF generator.

Figure 2:
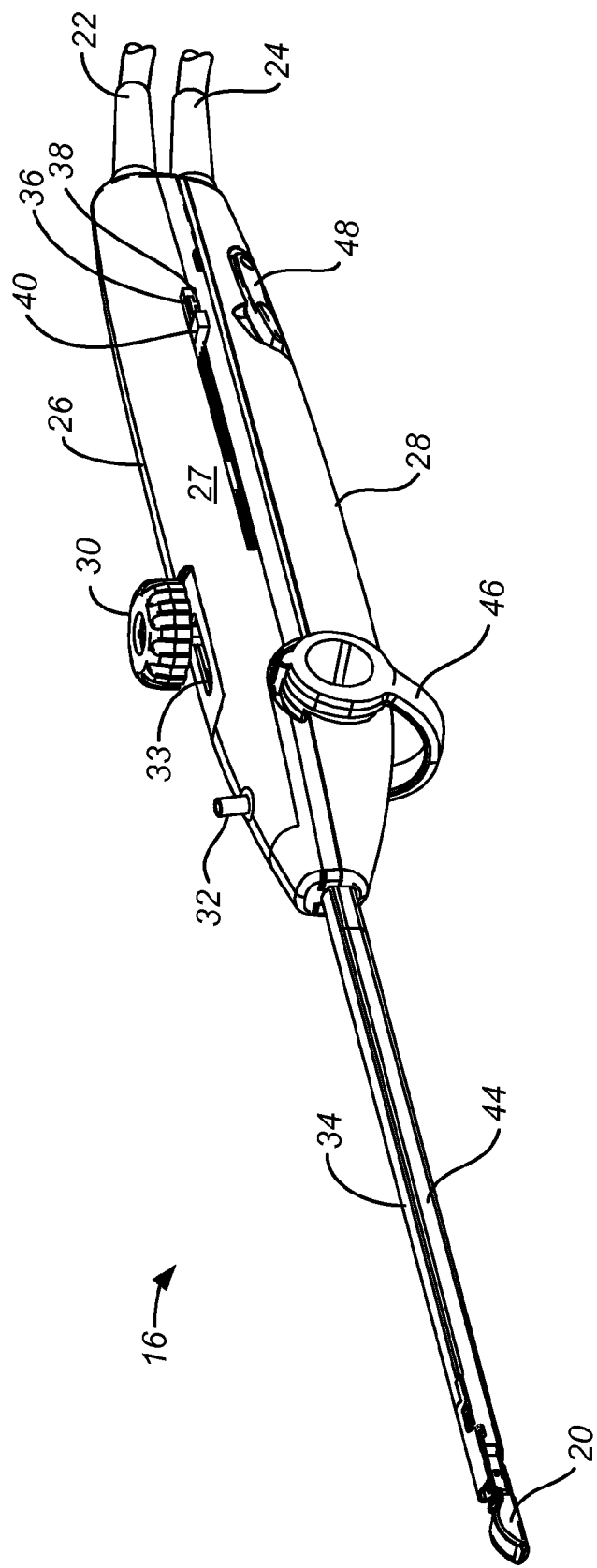
FIG. 2 is a perspective view of the treatment probe of the present invention.

Referring now to FIGS. 2 and 3, the treatment probe 16 comprises a needle component 26 and an imaging component 28. The needle component and imaging component are constructed as separate units or assemblies which may be removably attached to each other for use. After use, the needle component may be separated and will typically be discarded while the imaging component will be sterilized for reuse. The treatment probe 16 is shown in its fully assembled configuration in FIG. 2 and is shown in its disassembled configuration in FIG. 3. In other embodiments of the present invention, the needle component and the imaging component could be combined in a single, integrated handle unit.

The needle component 26 comprises a handle portion 27 having a slidably mounted targeting knob 30 on its upper surface. The targeting knob 30 controls the positioning of internal stops within the handle which are monitored by the controller 12 (FIG. 1) in order to calculate the size and position of the boundaries of the targeting region and/or the safety region which are shown on the display 14. The stops will also serve to physically limit deployment of the needle 56 and optionally tines 57, as will be described in more detail below.

The needle 56 is deployed from the needle shaft 34, and the needle and optional tines together form a needle structure which may be constructed, for example, as previously described in commonly owned U.S. Pat. Nos. 8,206,300 and 8,262,574, the full disclosures of which are incorporated herein by reference.

The handle portion 27 of the needle component 26 further includes a fluid injection port 32 which allows saline or other fluids to be injected through the needle shaft 34 into a target region in the tissue being treated, such as the uterus. The needle handle 27 also includes a needle slide 36, a needle release 38, and a tine slide 40 which are used to deploy the needle 56 and tines 57, as will be described in more detail below. The imaging cord 24 is attachable at a proximal end of the handle portion 27 of the imaging component 28 for connection to the controller 12, as previously described.

The imaging component 28 comprises a handle portion 29 and an imaging shaft 44. A deflection lever 46 on the handle portion 29 can be retracted in order to downwardly deflect the imaging transducer 20, as shown in broken line in FIG. 3. A needle component release lever 48 is coupled to a pair of latches 50 which engage hooks 52 on a bottom surface of the handle portion 27 of the needle component 26. The needle component 26 may be releasably attached to the imaging component 28 by first capturing a pair of wings 58 (only one of which is shown in FIG. 3) on the needle shaft 34 beneath hooks 60 on the imaging shaft 44, as shown in FIG. 3A. A bottom surface of the needle handle portion 27 may then be brought down over an upper surface of the imaging handle portion 29 so that the hooks 52 engage the latches 50 to form a complete assembly of the treatment probe 16, where the handle portions together form a complete handle, for use in a procedure. After use, the needle component release lever 48 may be pulled in order to release the hooks 52 from the latches 50, allowing the handle portions 27 and 29 to be separated.

In use, as will be described in more detail below, the targeting knob 30 is used to both position (translate) and adjust the size of a virtual treatment region which is projected onto the display 14 of the system 10. The knob 30 may be moved distally and proximally in a slot on an upper surface of the handle portion 27 in order to translate the position of the treatment/safety region on the image, and the knob may also be rotated in order to adjust the size of the boundary of the treatment/safety region. Sliding and rotating the knob 30 will also adjust the position of mechanical stops in the handle portion 27 which limit the deployment of the needle 56 and tines 57 so that, once the virtual boundaries of the treatment/safety region have been selected on the real-time image, the needle and tines may be automatically advanced to the corresponding deployment positions by moving the needle slide 36 and tine slide 40 until their movement is arrested by the stops. The position of the treatment/safety region is also dependent on the location at which the physician holds the treatment probe 16 within the target tissue. Thus, advancement of the needle and tines using the slides 36 and 40 will result in the proper placement of the needle and tines within the target tissue only if the treatment probe position is held steady from the time the stops are set until advancement of the needle/tines is completed. In preferred embodiments, rotating the knob 30 will also determine the length of and/or power delivery during a treatment protocol. Thus, the knob may be used to virtually size the treatment/safety region based not only on the degree to which the tines have been advanced, but also the amount of energy which is being delivered to the target tissue.

Referring now to FIGS. 4A through 4F, construction of the needle handle portion 27 and internal components thereof will be described in greater detail. Note that the orientation of the needle component 26 is reversed relative to that shown in FIGS. 2 and 3 so that the needle shaft 34 is extending to the right in FIGS. 4A-4F rather than to the left as shown in FIGS. 2 and 3. The handle portion 27 of the needle component 26 is shown with its upper portion partially removed in each of FIGS. 4A through 4F. A needle stop housing 64 is slidably mounted in the housing with a shaft 31 of knob 30 traveling in a slot 33 (FIG. 2) as the housing 64 is translated.

A needle carriage 68 is also slidably mounted in the housing portion 27 and carries a tine stop 66 which is mounted on a lead screw 72. The knob 30 is coupled to the lead screw 72 by a gear train 71 which turns a drive shaft 70 which is slidably inserted into the lead screw 72. The drive shaft 70 will have an asymmetric cross-section which slides into and out of a mating passage axially aligned in the lead screw 72. Thus, the knob 30 can be used to rotate the lead screw independent of the relative axial positions of the needle stop housing 64 and the needle carriage 68.

As will be explained in more detail below, treatment probe 16 has a number of interlock features which prevent unintentional actuation of the stops, needle, and tines as well as requiring that the stop positions and needle/tine actuations be performed in a proper order. As part of this interlock system, pawls 74 are provided on a side of the needle stop housing 64 such that the pawls 74 engage with a rack of teeth 132 (FIG. 8) on the inside of the handle portion 27 housing to prevent motion of the needle stop housing 64 unless the pawls are disengaged. The pawls are disengaged by depressing the knob 30 which allows the knob to be moved distally and proximally on the handle portion 27 in order to reposition the needle stop housing 64 in the housing portion 27. When the knob is released, the pawls 74 re-engage, locking the needle stop housing 64 in place relative to the handle portion 27.

Similarly, pawls 76 (FIGS. 4A and 4B) are provided on the needle carriage 68. These pawls also engage a rack of teeth 134 (FIG. 8) on the inside of the housing of handle portion 27. The pawls 76 are normally engaged, locking the carriage 68 in place, but may be disengaged by pressing on the T-shaped release 38, allowing the carriage to be pushed forward in order to distally advance the needle 56 which has a proximal end (not shown) carried by the carriage. The tines 57 are advanced from the needle 56 by the tine slide 40, as will be described below.

As shown in FIG. 4B, the positions of the needle stop housing 64 and the tine stop 66 are sensed by the needle position sensor 78 and the tine position sensor 80, respectively. These sensors are typically rheostats with a change of position resulting in a change of resistance which is sensed by the controller 12, but other absolute position feedback devices, such as. LVDT, quadrature encoders or the like could also be used. Thus, prior to deployment of the needle or tines, the positions of the needle stop housing 64 and tine stop 66 may be tracked in real time by the controller 12 and the calculated treatment and/or safety boundaries displayed on the display unit 14 as the position of the needle stop housing is adjusted and the knob 30 rotated to adjust the position of the tine stop. Of course, the actual positions of the stops could also be visually or numerically shown on the display 14. Prior to any actual deployment of the needle and tines, the physician will have visual information confirming the treatment/safety region boundaries which will result from the needle/tine deployment which has been set into the treatment probe by adjusting the needle and tine stops.

A particular advantage of this method and system is that the physician can manipulate the treatment/safety boundaries over the target anatomy by either moving the boundaries relative to (or within) the real-time image by manipulating (sliding and turning) knob 30 or moving the entire real-time image with respect to the target anatomy by manipulating the entire treatment probe 16 in order to get the treatment boundary over the tumor and keeping the safety boundary away from sensitive anatomy. So, before the physician advances any needles into the patient tissue, they can confirm in advance using the virtual targeting interface that the ablation will be effective and safe.

Referring to FIG. 4A, to virtually position the boundaries of the treatment/safety regions, the targeting knob 30 may be depressed and the knob moved distally in the direction of arrow 84, reaching the position shown in FIG. 4C. The physician will, of course, be able to move the needle stop housing both distally and proximally so long as the knob 30 is depressed, until the boundary of the treatment/safety region is properly located as shown on the visual display 14. Once properly positioned, the knob 30 is partially depressed to disengage rotation lock 110 (FIG. 6B), and the knob may be rotated as shown by arrow 86 to position the tine stop 66. More specifically, rotation of knob 30 rotates drive shaft 70 via the gear train 71. The drive shaft, in turn, rotates lead screw 72 which moves the tine stop 66 distally as shown by arrow 88 in FIG. 4D. Knob 30 can, of course, be rotated in either direction in order to reposition the tine stop 66 distally or proximally, which repositioning causes the "virtual" boundary projected on display 14 to expand or contract, respectively (FIG. 4D). Once the needle stop housing 64 and the tine stop 66 are in their desired positions (based on the virtual or projected images of the treatment/safety boundary on display 14), the treating physician can then physically advance the needle and the tines to the positions preset by the needle stop housing and tine stop. Referring to FIG. 4D, the needle release 38 is pushed in to disengage the pawls 76 and allow the needle carriage 68 to be moved in the direction of arrow 88. The needle carriage 68 is advanced until hitting the needle stop housing 64 as shown in FIG. 4E. Such motion of the needle carriage, in turn, distally advances the needle 56 as shown in broken line in FIG. 3.

After the needle 56 has been advanced, the tines 57 may be advanced by manually pushing the tine slide 40 distally until the tine slide 40 hits the tine stop 66 as shown by arrow 90 in FIG. 4E. Once the slide 40 is positioned distally, as shown in FIG. 4F, the needle 56 and tines 57 will be deployed, as shown in FIG. 3. At this point the controller 12 detects that the needle 56 and tines 57 have been fully extended and the physician confirms that the ablation will be of the correct size and at a safe and effective location. The tine slide locking arm 120 releases the tine slide 40 when the needle carriage 68 engages the stop housing 64. Thus, the switch on the tine stop 66 can be active only if the tine slide 40 was first released when the needle carriage 68 engaged the stop housing 64, with the single microswitch 112 indicating that the needle 56 and the tines 57 are in their proper positions.

Figure 5A:
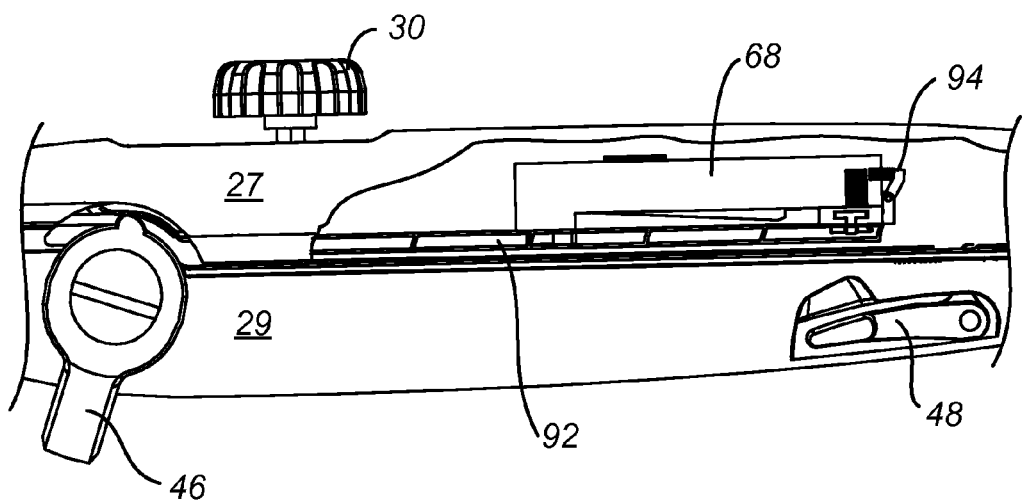
FIGS. 5A and 5B illustrate an interlock mechanism which prevents deployment of the needle structure prior to deflection of an imaging array on the imaging component of the probe.
Figure 5B:
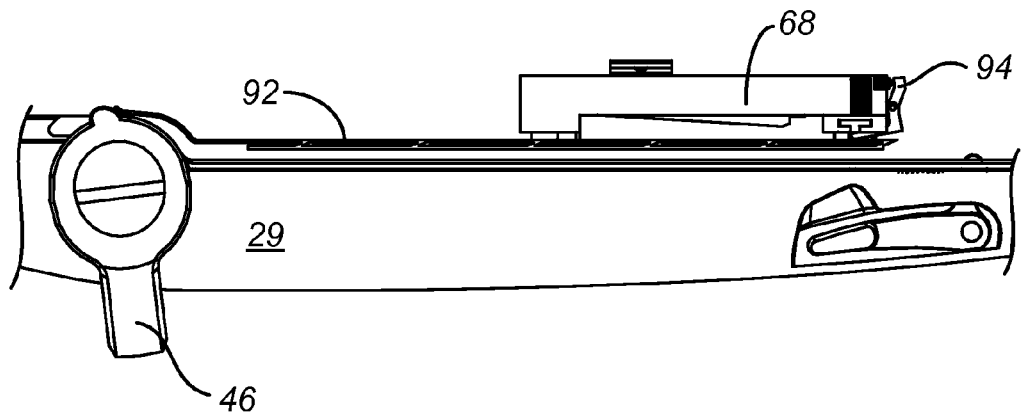

Referring now to FIGS. 5A and 5B, an interlock assembly for preventing motion of the needle carriage 68 prior to deflection of the image transducer 20 (FIGS. 2 and 3) will be explained. The transducer deflection lever 46 is initially pushed forwardly as shown in FIG. 5A, where the transducer 20 is in its axially aligned configuration, as shown in FIGS. 2 and 3. It will be appreciated that needle advancement while the transducer 20 is aligned axially would likely damage the transducer. To avoid such damage, as it is retracted, the lever 46 engages a four bar linkage 92 which is coupled to an angle lock 94 which prevents movement of the needle carriage 68. When the lever 46 is pulled proximally, however, to deflect the transducer 20 (as shown in broken line in FIG. 3), the four bar linkage is allowed to collapse and disengage the angle lock 94, as shown in FIG. 5B. In this configuration, the needle carriage 68 is free to be advanced and retracted. In other embodiments, a leveraged or pivoting beam could replace the four bar linkage.

Figure 6A:
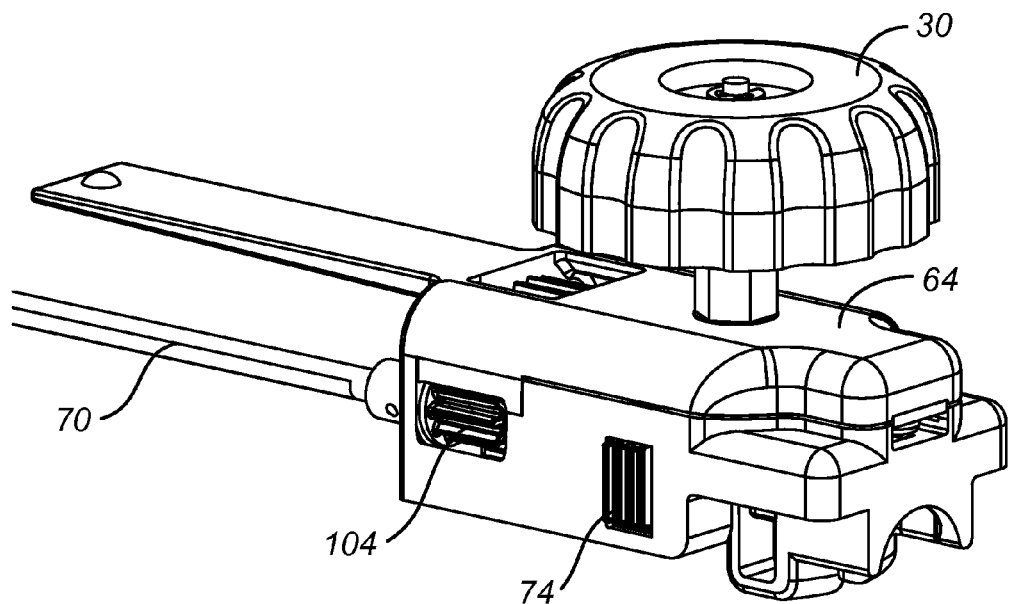
FIGS. 6A and 6B illustrate a gear train mounted on the needle stop housing used to deploy a needle and a plurality of tines of the needle structure.
Figure 6B:
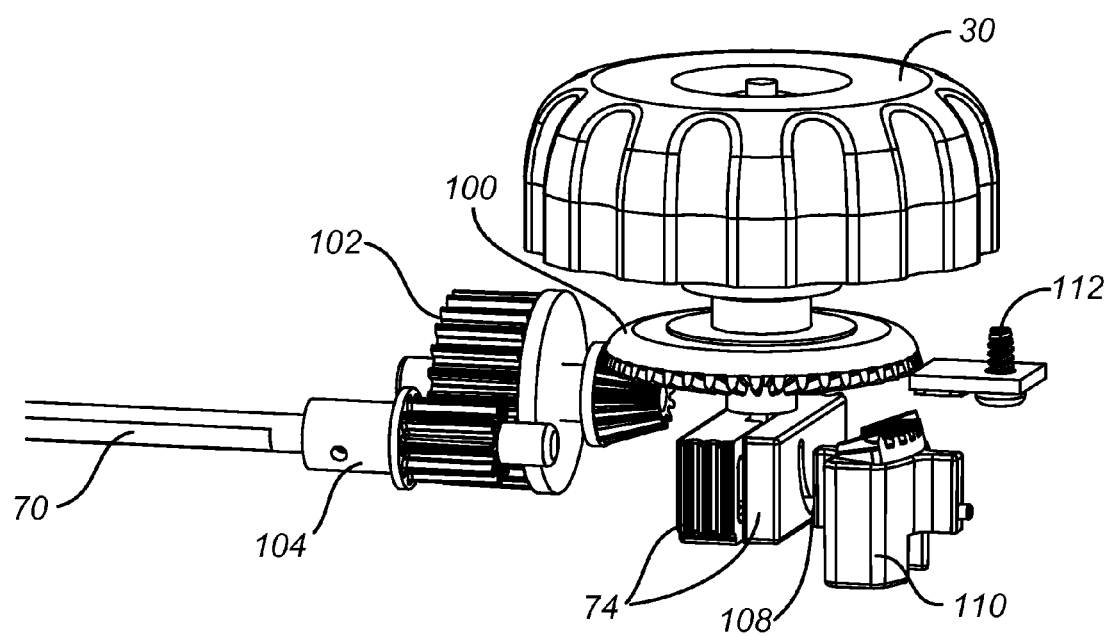

Details of the gear train which allows the knob 30 to rotate to the drive shaft 70 are shown in FIGS. 6A and 6B. The knob is attached to bevel gear 100 which rotates a bevel/spur combination gear 102 which in turn drives the spur gear 104 attached to the drive shaft 70. Depressing the knob 30 retracts the pawls 74 through interaction with dowel pin 108 which is moved up and down by the knob 30 and rides in slots or channels in the pawl surfaces. A rotation lock 110 is provided and engages the bevel gear to prevent rotation of the knob. A microswitch 112 is provided which signals to the controller when the rotation lock 110 and pawls 74 are engaged.

Figure 6C:
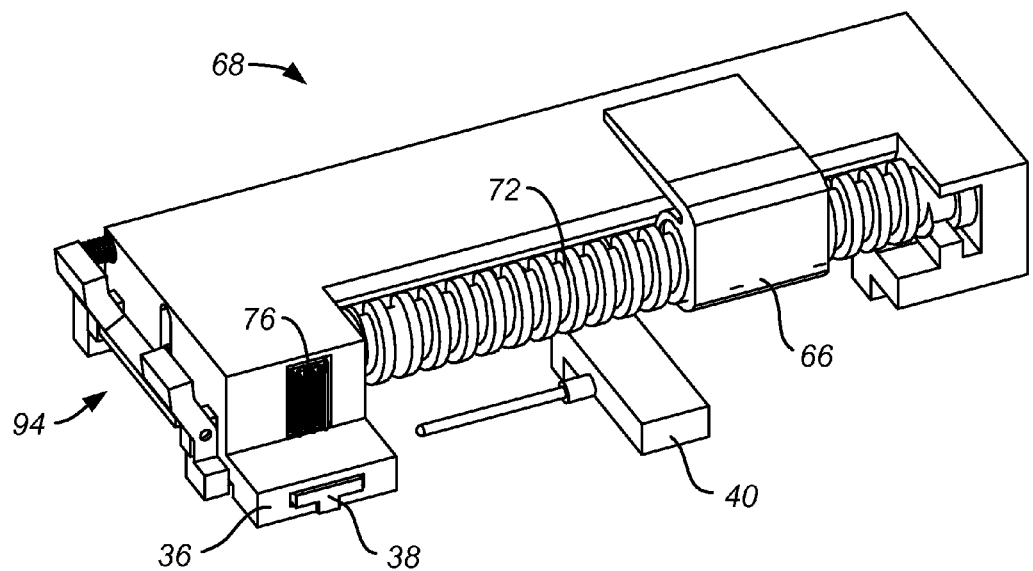
FIGS. 6C and 6D illustrate details of the needle carriage.
Figure 6D:
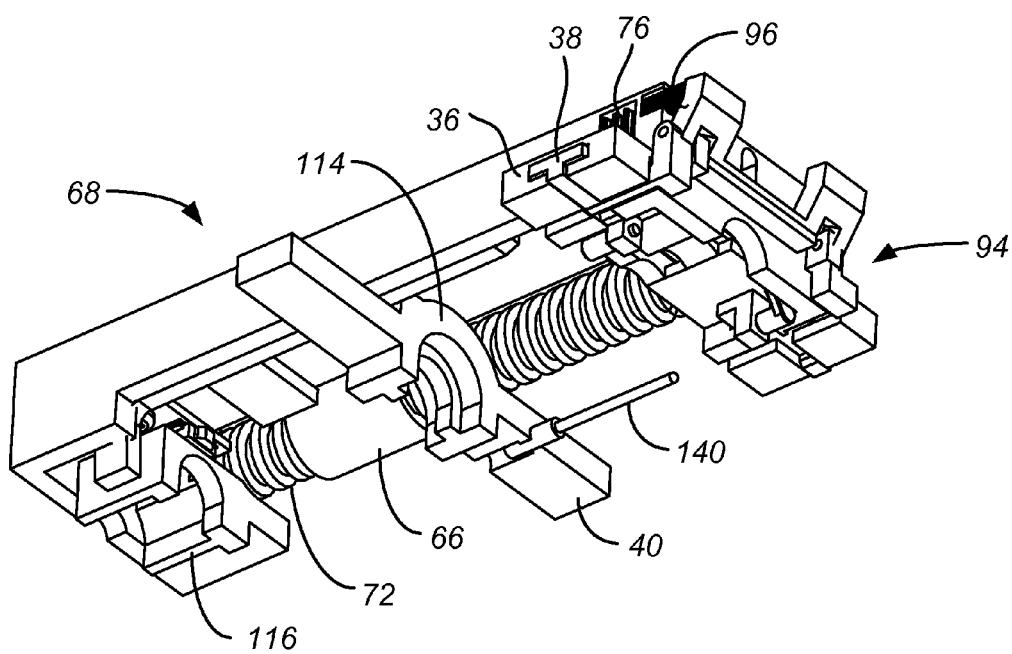

Referring now to FIGS. 6C and 6D, more details of the needle carriage 68 will be described. FIG. 6C is a top view of the needle carriage 68, generally as shown in previous figures. FIG. 6D is a bottom view of the needle carriage showing details not previously visible. The angle lock 94 translates an arm 96 which allows or prevents the needle release 38 from being actuated. As shown in FIG. 6D, the angle lock 94 is engaged (as shown in FIG. 5A). By retracting lever 46 (FIG. 5B), the angle lock 94 would disengage to withdraw the arm 96 to allow the needle release 38 to be depressed. The needle release 38, in turn, retracts pawls 76 which disengage with locking teeth 134 on handle portion 27.

A bracket 114 on the tine slide 40 engages with a shaft (not shown) which advances the tines within the needle, as will be described below. Similarly, a bracket 116 fixed to the needle carriage 68 engages a proximal end of the needle (not shown in FIG. 6D) which will advance the needle as the carriage is advanced.

One additional lock out is shown in FIG. 6D. A spring loaded plunger 140 projects out a back of tine slide 40. When the tine slide 40 is pushed up against the needle slide 36, (i.e., when the tines are not deployed), the spring loaded plunger 140 actuates the angle lock 94 and engages the arm 96 to lock out the needle release 38. When the tine slide 40 is moved away from the needle slide 36, the plunger 140 disengages the angle lock 94 and the arm 96 unlocks the needle release 38. Of course, other lock out mechanisms could be employed. For example, the tine slide 40 could engage a simple lever that directly interfaces with the needle release 68 without using a spring loaded plunger 140.

Figure 7A:
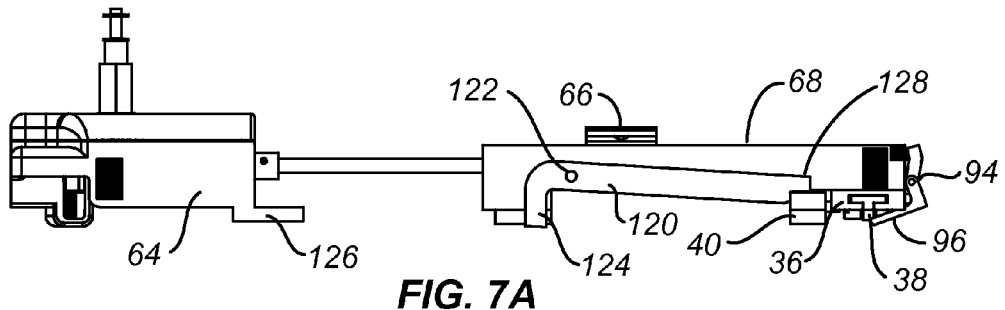
FIGS. 7A through 7C show relative movement of the needle carriage and needle stop housing.
Figures 7B, 7C:
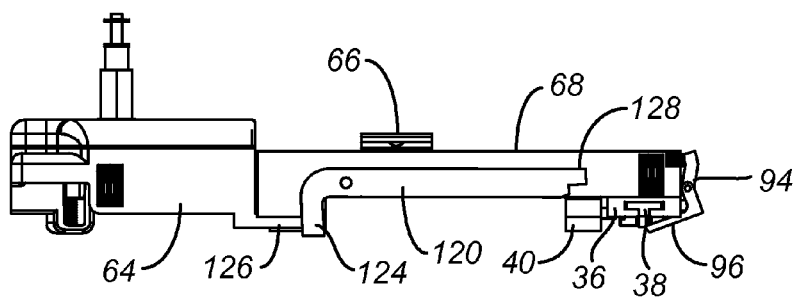

Referring now to FIGS. 7A through 7C, a mechanism for selectably locking the tine slide 40 prior to advancing the needle carriage 68 will be described. A tine locking arm 120 is attached via a pivot 122 on a side of the needle carriage 68, as shown in FIG. 7A. A side arm 124 of the locking arm 120 is disposed to engage a bar 126 fixed to the end of the needle stop housing 64 which engages the needle carriage when the needle carriage is fully advanced. As the needle carriage 68 is advanced distally (to the left in FIGS. 7A and 7B) to deploy the needle, the bar 126 on needle stop housing 64 will engage the side arm 124 on the tine locking arm 120. Such engagement will cause the locking arm to rotate in a counter-clockwise direction, thus raising a locking end 128 of the bar from an engagement configuration (FIG. 7A) to a non-engagement configuration (FIG. 7B) such that the tine slide 40 may be advanced distally only after the needle carriage has been fully advanced. In this way, accidental, premature deployment of the tines may be prevented.

One skilled in the art will appreciate that there are many ways to design the lock outs that control the order of deployment of the components of the treatment probe. For example, the bar 126 could be integrated into side 124 rather than 64. The lockout 120 could be designed as a leaf spring so that it does not rely on gravity to engage locking end 128 with tine slide 40.

FIGS. 7B and 7C illustrate how the arm 96 of the angle lock 94 is raised in order to lock the needle release 38 to prevent accidental needle deployment.

Figure 8:
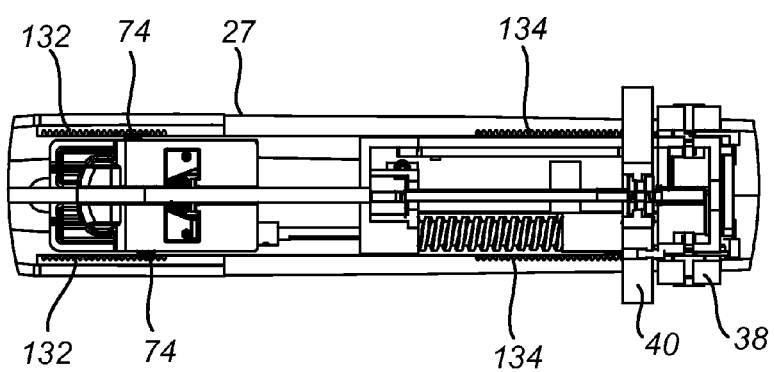
FIG. 8 is a bottom view of the needle carriage.

Referring now to FIG. 8, inner teeth 132 and 134 are formed on an interior surface of the housing portion 27 of the needle component 26 of the treatment probe 16. The teeth 132 selectively engage pawls 74 disposed on the needle stop housing 64, as previously described. The teeth 134 selectively engage pawls 76 (not shown in FIG. 8) which are on the needle carriage 68.

Figure 9:
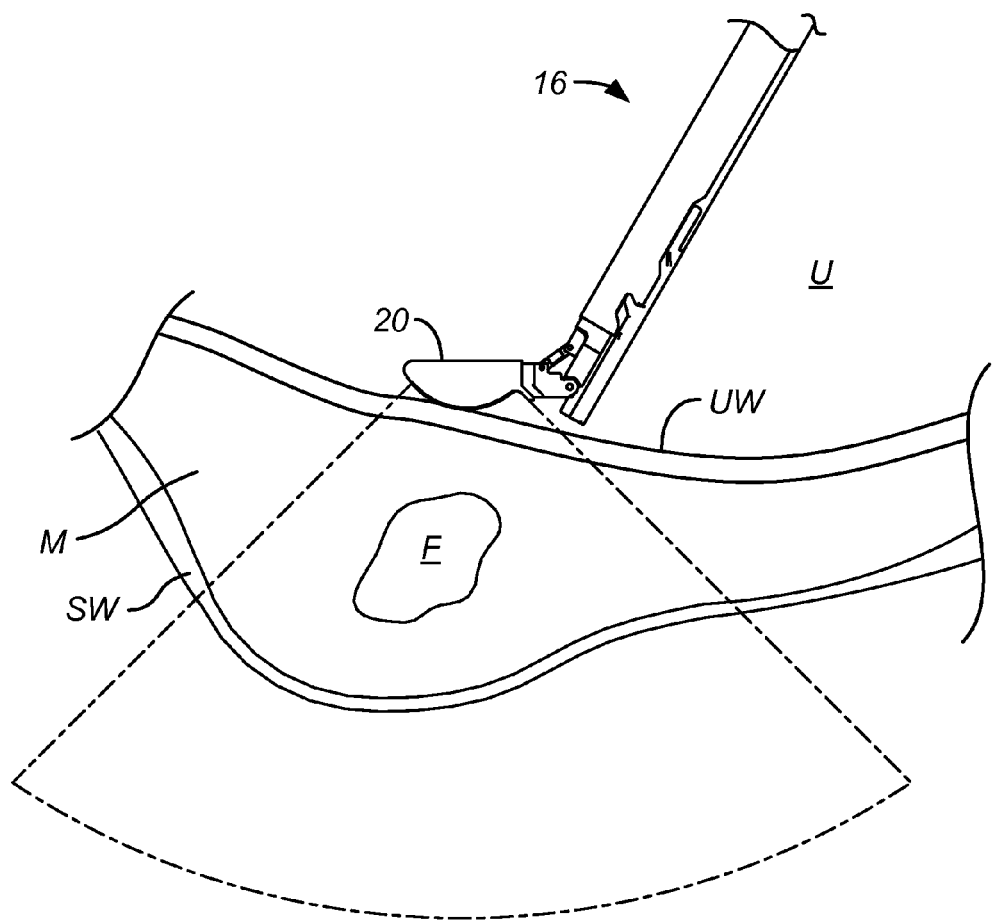
FIG. 9 illustrates a distal portion of the treatment probe introduced into a uterine cavity to image a fibroid in the myometrium.

Referring now to FIG. 9, the system 10 of the present invention can be used to treat a fibroid F located in the myometrium M in a uterus U beneath a uterine wall UW (the endometrium) and surrounded by the serosal wall SW. The treatment probe 16 can be introduced transvaginally and transcervically (or alternately laparoscopically) to the uterus, and the imaging transducer 20 deployed to image the fibroid within a field of view indicated by the broken lines.

Figure 10A:
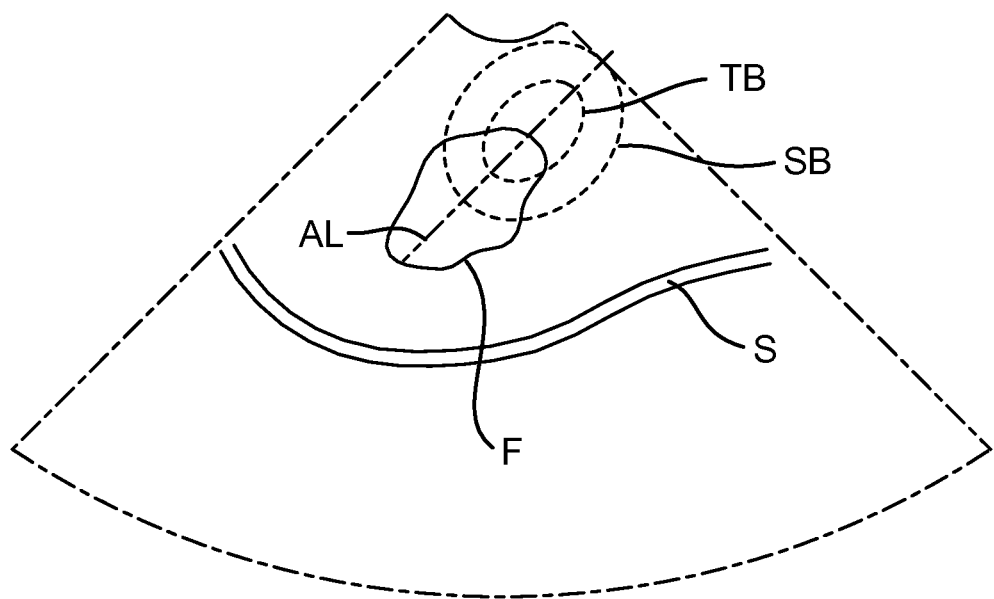
Figure 10B:
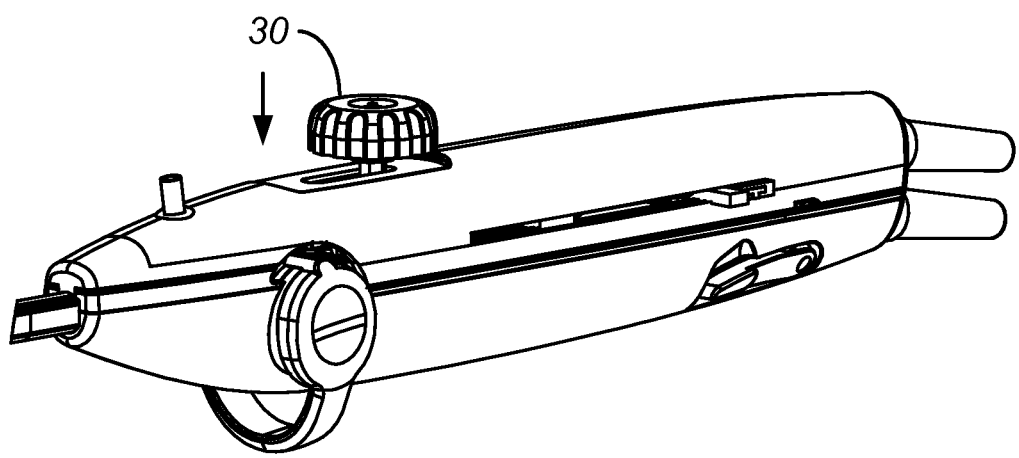

Once the fibroid is located on the display 14, as shown in FIG. 10A, the controls on the handle will be used to locate and size both a treatment boundary TB and a safety boundary SB. Initially, as shown in FIG. 10A, the virtual boundary lines TB and SB are neither positioned over the fibroid nor properly sized to treat the fibroid. Prior to actual needle and tine deployment, the physician will want to both position and size the boundaries TB and SB for proper treatment. As the imaging transducer 20 is already positioned against the uterine wall UW the only way to advance the treatment and safety boundaries is to move the boundaries forward by depressing the targeting knob 30, as shown in FIG. 10B, and then distally advancing the knob as shown in FIG. 11B. This will cause the treatment and safety boundaries TB and SB to move forwardly along the axis line AL. This causes the virtual boundaries on the real-time image display 14 to move over the image of the fibroid, as shown in FIG. 11A.

Figure 11A:
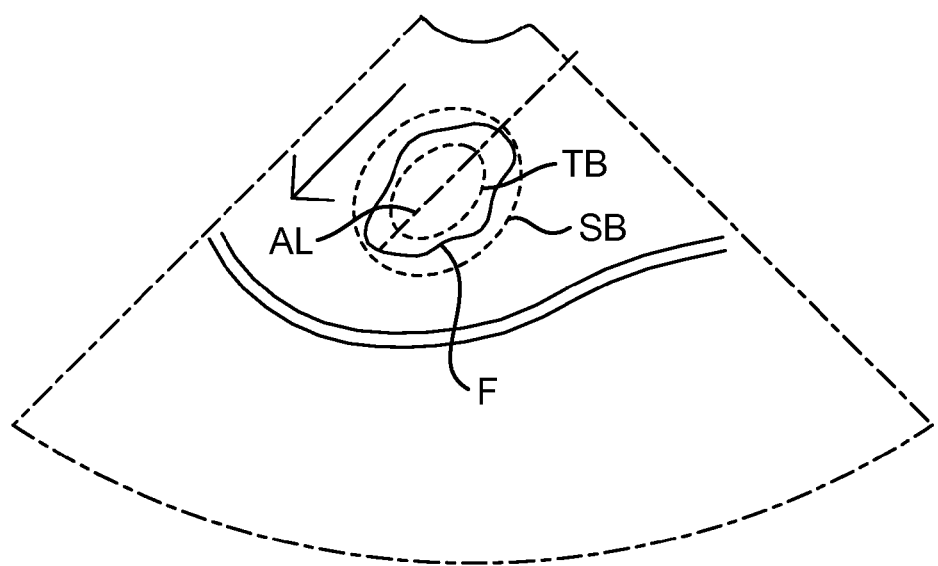
Figure 11B:
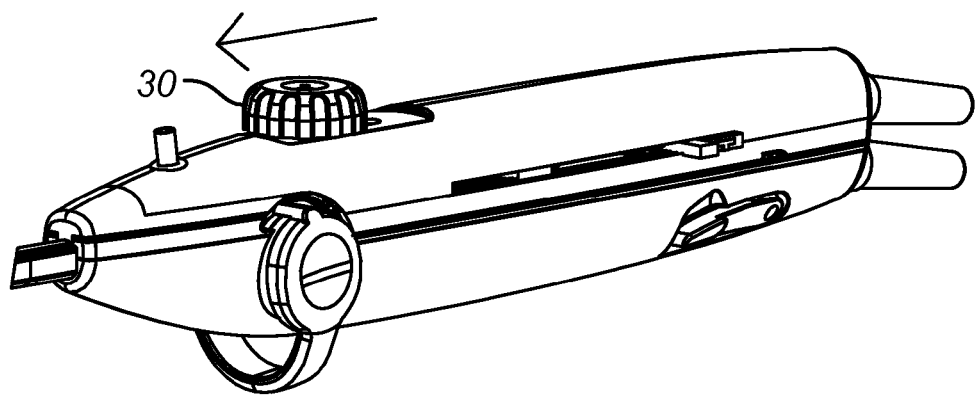
Figure 12A:
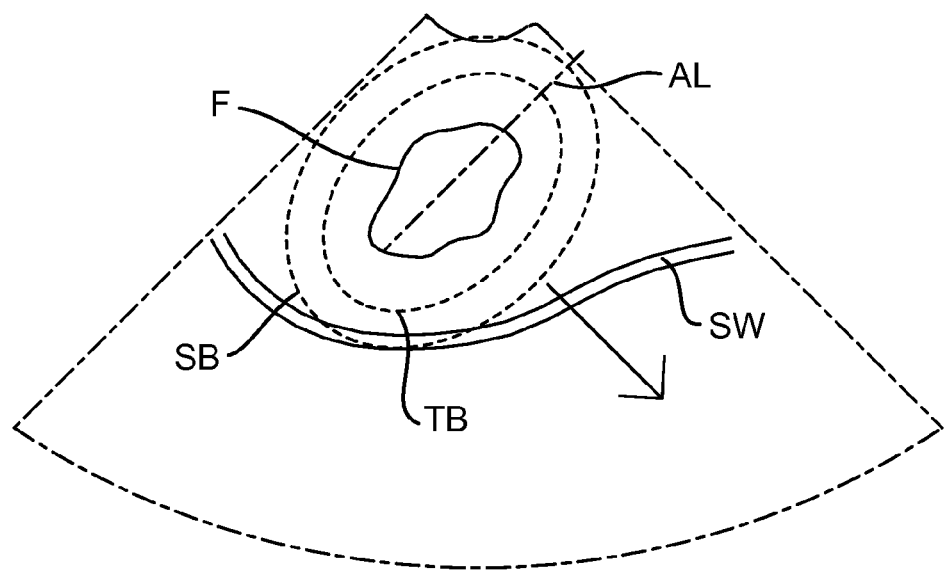
Figure 12B:
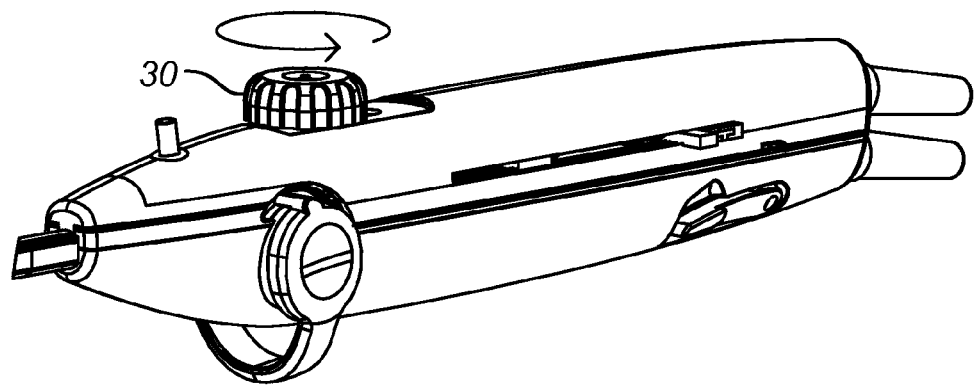
Figure 13A:
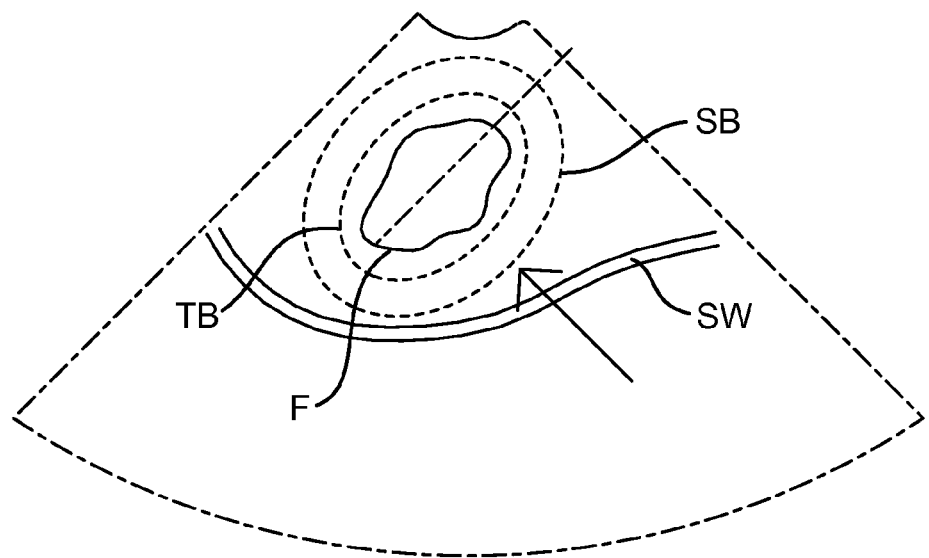
Figure 13B:
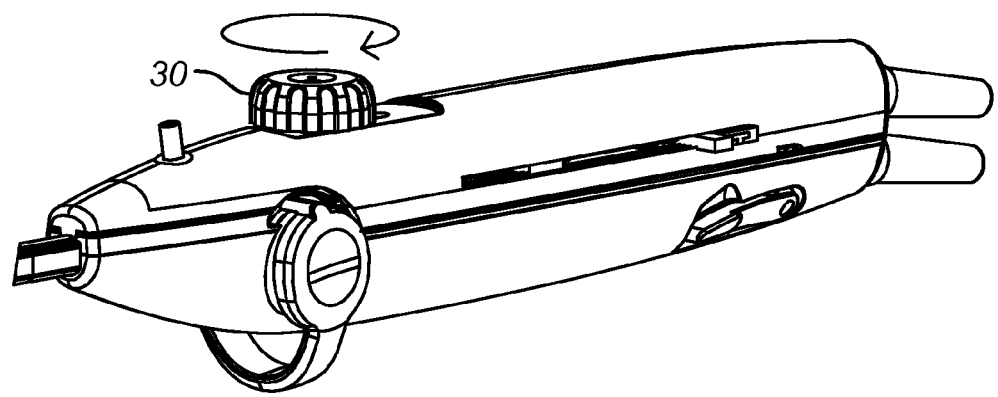

As shown in FIG. 11A, however, the size of the treatment boundary TB is insufficient to treat the fibroid since the boundary does not extend over the image of the fibroid. Thus, it will be necessary to enlarge the treatment boundary TB by rotating the targeting knob 30, as shown in FIG. 12B. This enlarges both the treatment boundary TB and the safety boundary SB, as shown in FIG. 12A. While the enlarged virtual treatment boundary TB is now sufficient to treat the fibroid, the safety boundary SB has extended over the serosal wall SW, as also shown in FIG. 12A. Thus, there is risk that the treatment would affect more sensitive tissue surrounding the uterus, and it is necessary that the virtual safety boundary SB be retracted by turning the targeting knob 30 in an opposite direction, as shown in FIG. 13B. This reduces the size of both the safety and treatment boundaries SB and TB, as shown in FIG. 13A, and the physician has confirmation that the treatment will be effective because the treatment boundary TB completely surrounds the fibroid on the real-time image display, and that the treatment will be safe because the safety boundary SB is located within the myometrium M and does not cross the serosal wall SW on the real-time image display. In addition, the surgeon knows that the stops in the treatment probe are now appropriately set to deploy the needle and tines to achieve the treatment result shown by the virtual boundaries in FIG. 13A.

Figure 14A:
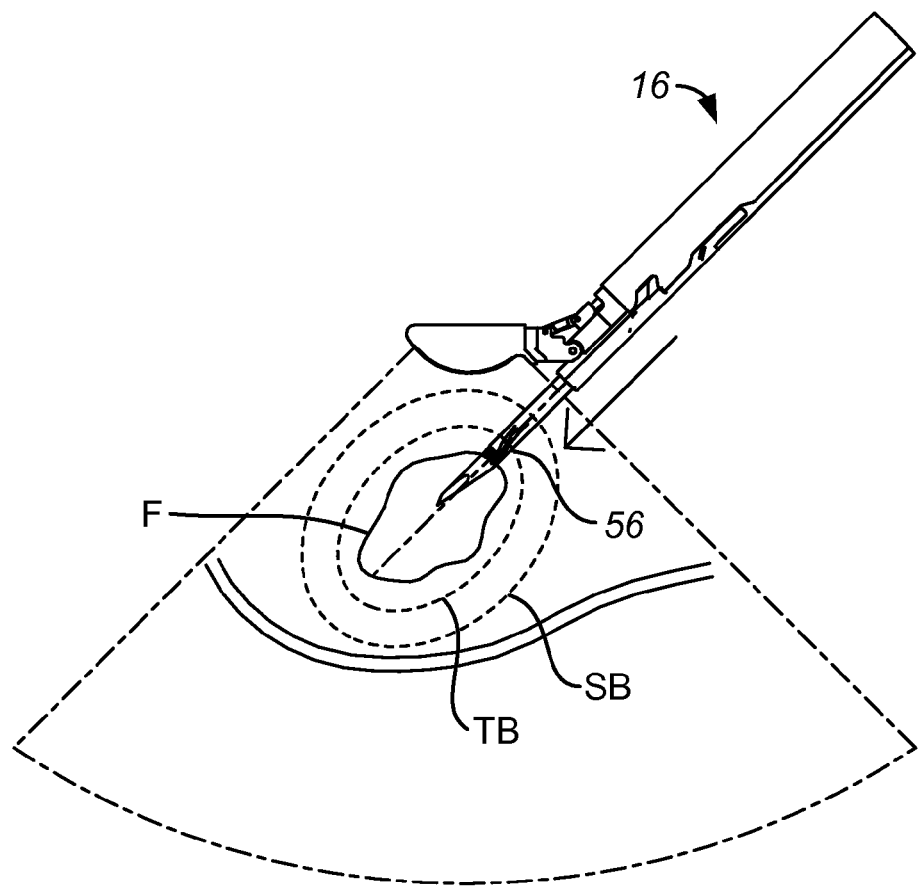
Figure 14B:
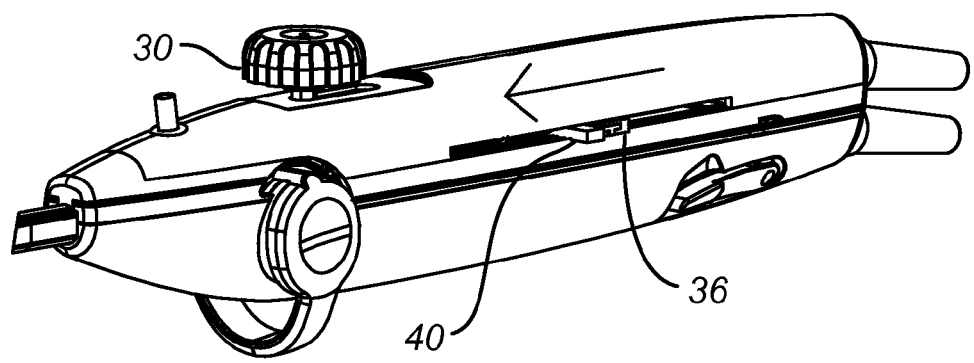

While holding the treatment probe 16 steady, the physician then advances the needle slide 36 (after depressing the release), as shown in FIG. 14B, causing the needle 56 to extend into the fibroid F, as shown in FIG. 14A. The illustration in 14A includes a representation of the treatment probe 16 which corresponds to the physical probe which is present in the patient. The remainder of FIG. 14A corresponds to the image present on the target display 14.

Figure 15A:
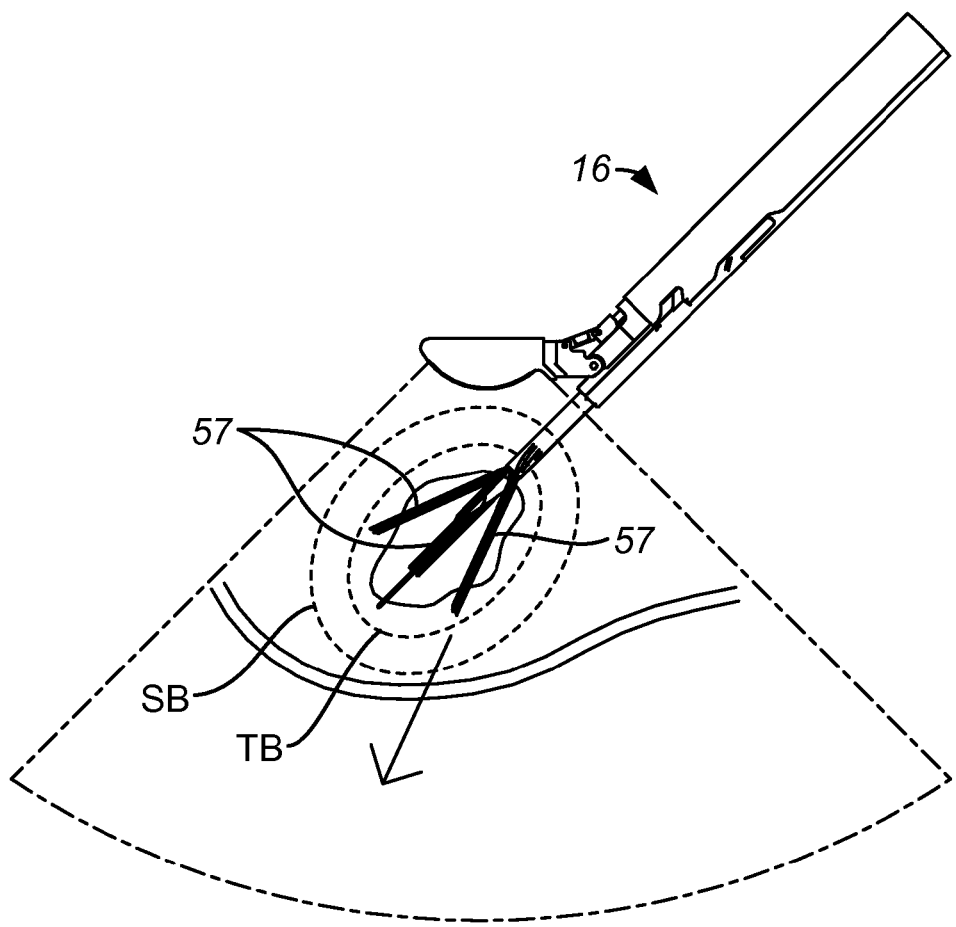
Figure 15B:
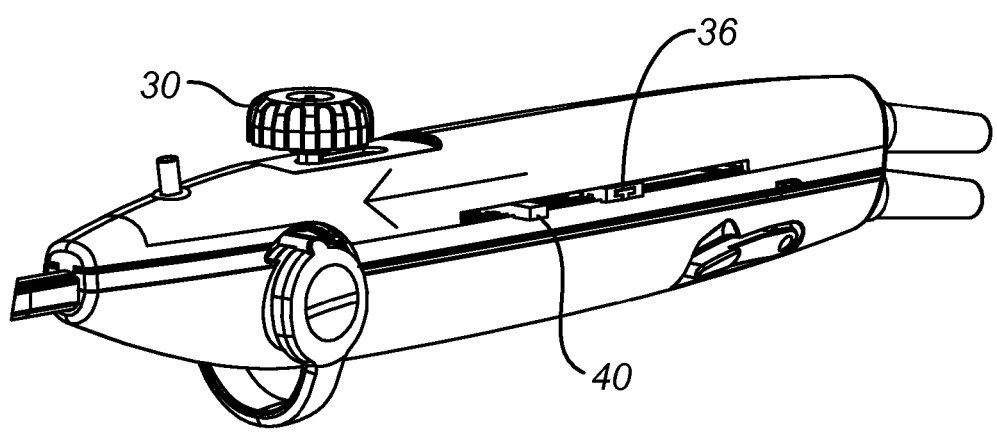

After needle 56 has been fully deployed as limited by the needle stop housing 64 in the treatment probe 16, the tines 57 may be deployed by advancing the tine slide 40 until it engages the tine stop 66, as shown in FIG. 15B. Optionally, the treatment probe 16 may be rotated about a central axis (typically aligned with the axis of the needle 56) to confirm the treatment and safety boundaries in all planes of view about the fibroid. Display 14 will show the position of the treatment and safety boundaries in real time relative to the target fibroid and serosa. The tines are then configured as shown in FIG. 15A, and power can be supplied to the tines (and optionally the needle) in order to achieve treatment within the boundary depicted by the virtual treatment boundary TB. Again, FIG. 15A mixes both the virtual image which would be present on the display 14 as well as the physical presence of the treatment probe 16.

Figure 16A:
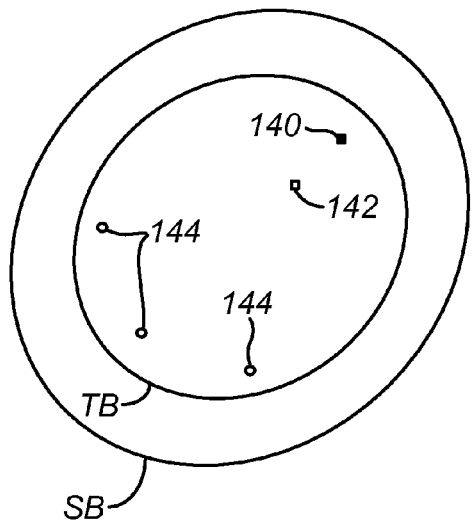
FIGS. 16A-16D illustrate the provision of fiducials or markers on the real-time image, where the fiducials or markers correspond to needle tip locations.

Referring now to FIG. 16A through 16D, the controller 12 can be programmed to display fiducials or markers on the image display 14, where the fiducials or markers represent particular locations on the "virtual" needle and/or tines. For example, as shown in FIG. 16A, marker 140 may represent a position on the needle 56, for example, the location from which the tines will diverge. An additional marker 142 may be provided which represents the tip of the needle. A plurality of additional markers 144 may represent the tips of the tines. The use of fiducials or markers 142 and 144 help the physician confirm that the actual needle and tines are deployed correctly. The physician should be able to observe the real-time images of the actual needle and tines during deployment, and the associated tips should move until the needle tip reaches marker 142 and the tine tips hit markers 144. (or alternatively the alternative targets in FIGS. 16B-16D as described below).

Figure 16B:
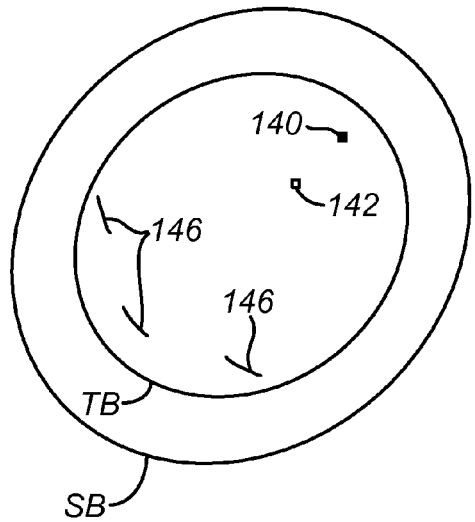
Figure 16C:
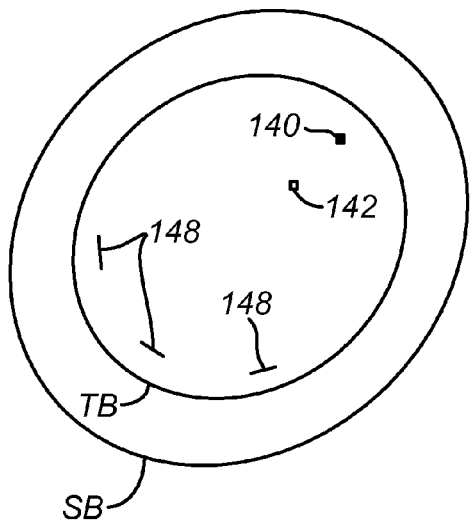
Figure 16D:
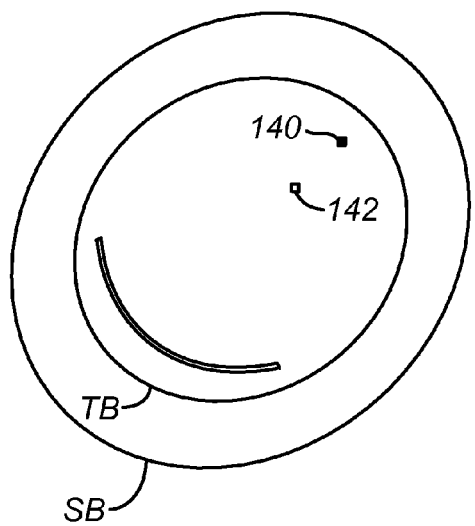

FIG. 16B is similar to FIG. 16A, except that the fiducials representing the tips of the tines are depicted as arcs 146 which represent a range of possible positions for the distal tips of each tine. Such additional information may be useful for the physician when determining both adequacy of treatment and safety risks. As shown in FIG. 16B, each arc has a radius equal to the theoretical electrode deployment length. As shown in FIG. 16C, arcs 148 all have the same radius measured from the origin located at the tip 142. Finally, in FIG. 16D, the arcs of FIG. 16C are joined into a continuous arc which is intended to present a more clear visual presentation for use by the physician.

Figure 17C:
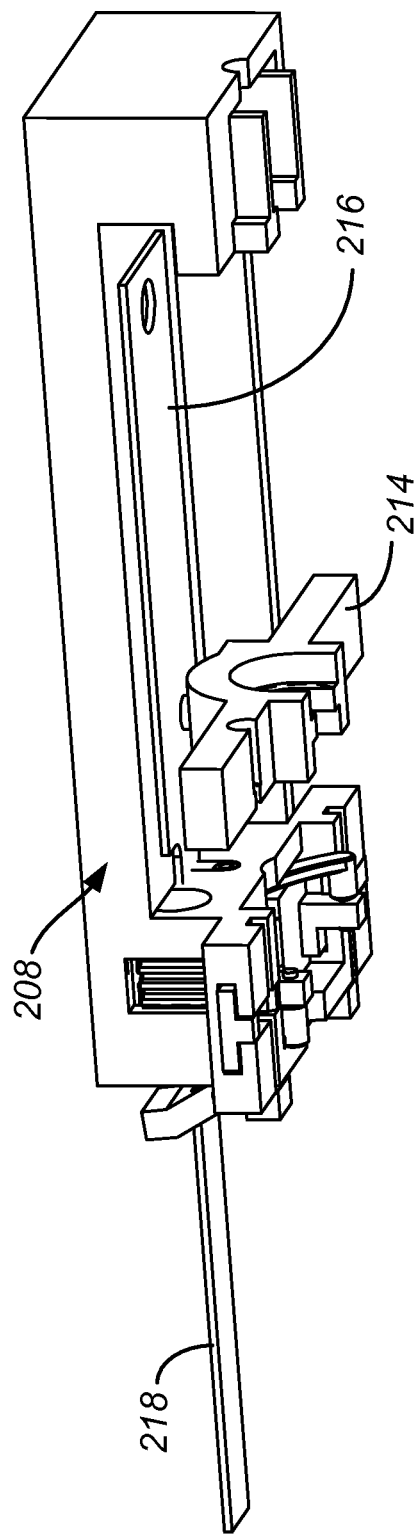

As described thus far, the illustrated embodiments of the needle housing have all included mechanisms for placing a needle stop and a tine stop for both adjusting the virtual images of the treatment and safety boundaries on the display screen and for subsequently positioning the actual needles and tines in the patient tissue for treatment. An alternative needle housing 202 which dispenses with the needle and tine stops is illustrated in FIGS. 17A-17C. The needle housing 202 includes both a treatment cord 204 and a needle shaft 206, both of which are generally the same in structure and purpose as described for previous embodiments, and the needle housing can be secured to and removed from an imaging housing 28 as described in the previous embodiments. A needle carriage 208 within the needle housing 202 and a tine slide 214 within the needle carriage 208 (FIG. 17C), in contrast, are freely positionable by the user and are not limited by stops or any other motion limiting mechanisms. Instead, the position of the needle carriage 208 is tracked by a needle carriage position sensor 210 on the bottom of the needle housing 202, as best seen in FIG. 17A. Similarly, the tine slide 214 is tracked through a position sensor 216 which is on an upper portion of the needle carriage 208, as best seen in FIG. 17C.

The physician or other user may virtually position the treatment boundary and/or the safety boundary on a display screen using an interface other than the control knob 30 as described for previous embodiments. For example, the treatment and/or safety boundaries may be positioned on a display screen having a real time image of the uterine anatomy using a keyboard, a mouse, a roller ball, a touch screen, voice activation, or any other conventional interface used with computer and other displays. The virtual treatment and/or safety boundaries will be set relative to the actual position of the needle shaft 206 which can be tracked by the system using the image of the shaft in tissue. After the physician is satisfied with the placement of the virtual treatment and/or safety boundaries, the physician can then manually advance the needle while the system controller monitors the advancement through the sensor 210 in the needle housing 202. Through visual, audible, or other means, the system can alert the physician when the needle has been advanced by the appropriate distance. After locking the needle, the user can then advance the tines manually while the controller monitors their position via the sensor 216. The system will again alert the physician when the tines have been deployed by the appropriate amount within the limits of the virtual treatment and/or safety boundaries. The system can then alert the physician that treatment may commence.

Figure 18A:
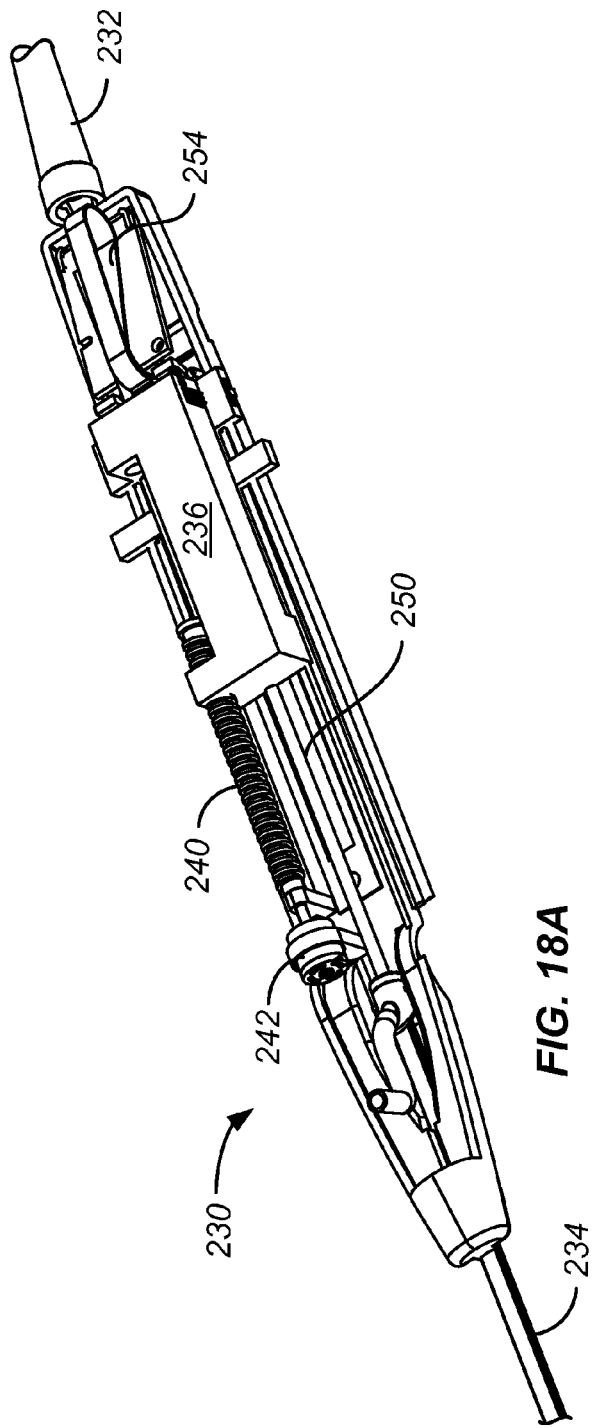
FIGS. 18A and 18B illustrate a further alternative embodiment of the needle housing of the present invention employing servo motors and drive screws for positioning both the needle carriage and the tine slide.
Figure 18B:
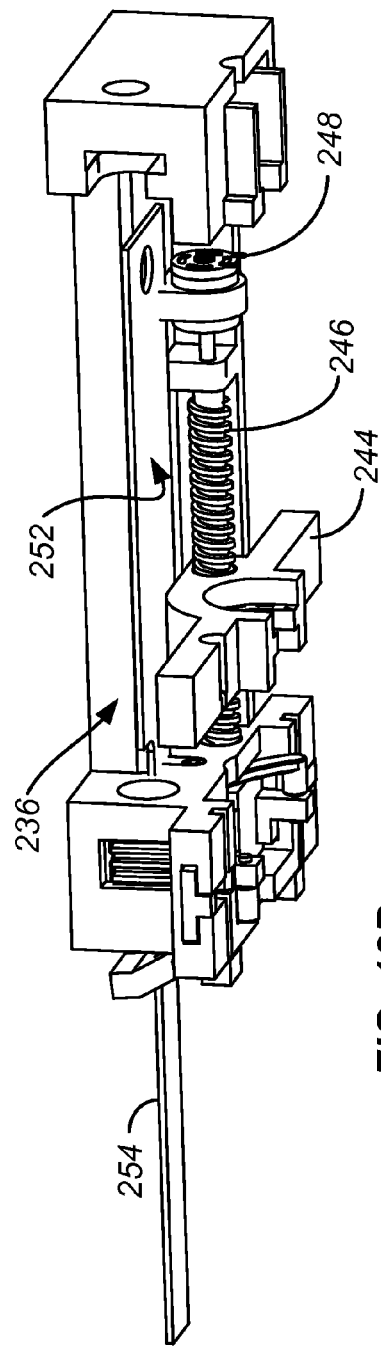

A still further alternative embodiment of a needle housing 230 is illustrated in FIGS. 18A and 18B. The needle housing 230 again includes a treatment cord 232 and a needle shaft 234 which are generally the same as those described for all previous embodiments. A needle carrier 236, however, differs from previous embodiments in that it is driven by a drive screw 240 which in turn is driven by a servo motor 242. The servo motor will be controlled by the system controller 12 based on information relating to the boundaries of the treatment region and/or safety region, which can be produced by any of the methods discussed previously.

Similarly, a tine slide 244 is driven by a tine slide drive screw 246, as best seen in FIG. 18B. The tine slide drive screw, in turn, is driven by a tine servo motor 248 which is also driven and controlled by the system controller. The needle carrier 236 may further comprise a needle carrier position sensor 250 and a tine slide position sensor 252, although such position sensors are not essential since the servo motors should provide accurate position data regarding the needle carrier 236 and the tine slide 244. The position sensors, however, are useful since they allow for initializing the positions and for confirming the positions during the needle and tine deployment operations. The tine slide position sensor 252 can be connected through a flexible connector strip 254.

Embodiments employing servo-driven needles and tines may be combined with most of the previously described embodiments, including both embodiments where the treatment and/or safety boundaries are determined virtually prior to needle deployment in those embodiments where the treatment and/or safety boundaries are determined while the needle structures are being deployed.

Figure 19:
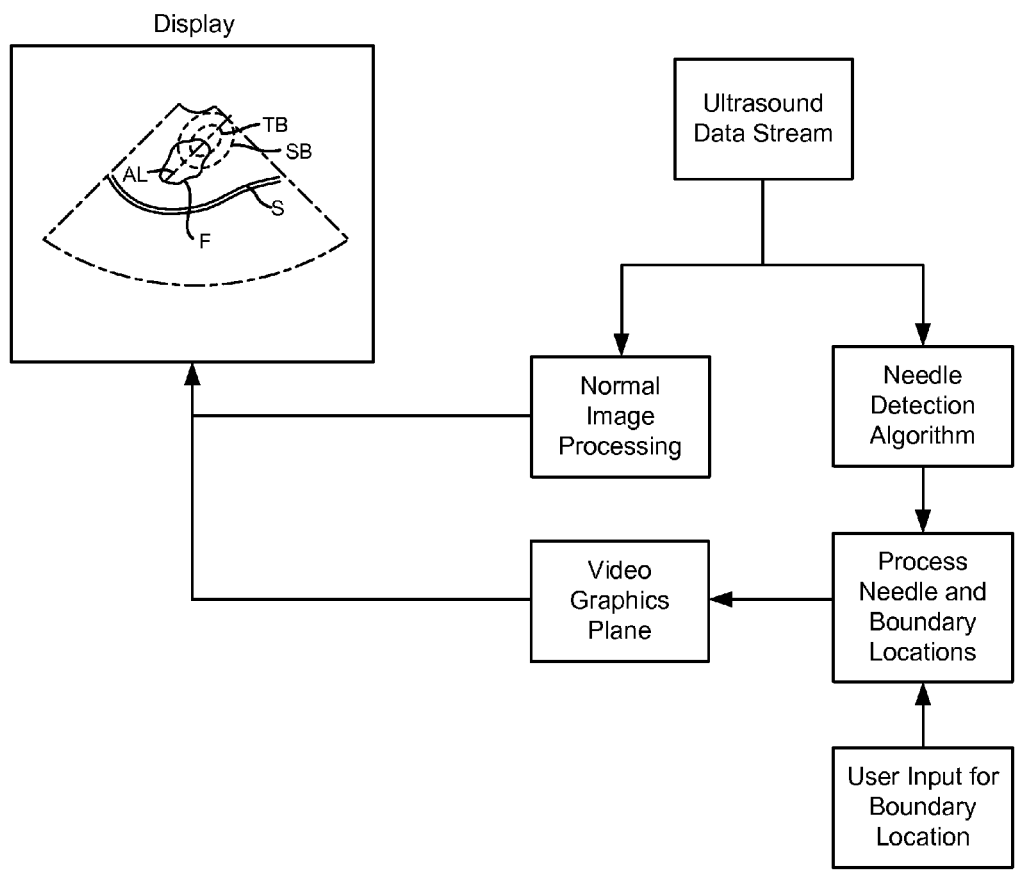
FIG. 19 illustrates a system diagram where real-time ultrasound image data is relied on to determine the positions of the needle structures of the present invention.

Referring now to FIG. 19, in certain embodiments of the present invention, the needle and/or tine positions may be determined based on the ultrasound image information rather than on information from the treatment probe configuration. As shown, an ultrasound data stream from the on-board imaging transducer provides both the normal image which is presented on the display and provides the needle image and location information to the system controller. The user inputs the boundary locations to the system controller by any of the ways described previously. The system controller can then calculate the treatment and/or boundary regions and compare those to the actual boundaries which would be obtained based on the monitored needle/tine positions.

Figure 20:
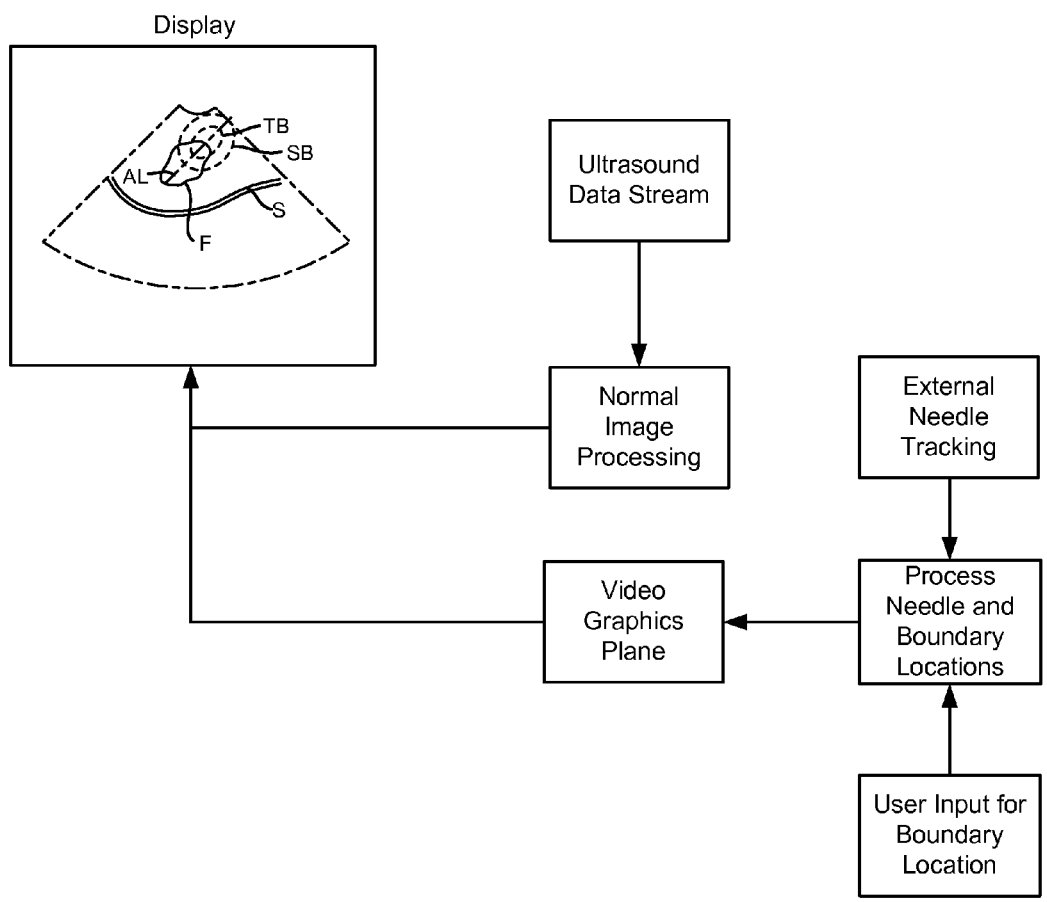
FIG. 20 illustrates a system diagram where external needle tracking data is used for tracking the needle position.

Referring now to FIG. 20, the systems and methods of the present invention can also rely on external needle tracking, such as the use of radio frequency tags, for tracking real-time needle position in tissue. The real-time data can then be relied on by the system controller to determine whether the needles remain within the boundaries so that both safe and effective treatment can be effected.

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the following claims define the scope of the invention and that methods and structures within the scope of these claims and their equivalents be covered thereby.

What is claimed is:

1. A method for deploying a needle structure in tissue, said method comprising:
positioning a probe having a deployable needle structure near an anatomical feature in the tissue;
providing a real time image of the tissue including the anatomical feature to be treated on a display connected to a controller;
projecting a treatment region and a safety region on the real time image prior to deploying the needle structure;
adjusting a size and a position of a boundary of at least one of the projected image of the treatment region and safety region on the real time image prior to deploying the needle structure, wherein adjusting the size and position of the projected boundary comprises adjusting a user interface connected to the controller; and
deploying the needle structure from the probe, wherein the needle structure is positioned relative to the probe and the tissue to provide treatment within the projected boundary after the projected boundary has been adjusted.

2. A method as in claim 1, wherein a position of the projected boundary is adjusted by manually repositioning the probe relative to the anatomical feature.

3. A method as in claim 1, wherein the interface comprises a keyboard, mouse, roller ball, or touch screen which is connected to the controller.

4. A method as in claim 1, wherein the interface is on the probe.

5. A method as in claim 4, wherein the interface on the probe also adjusts mechanically a needle deployment stop on the probe, wherein advancement of the needle to the needle deployment stop assures that the treatment region will be treated and that treatment will not extend beyond the safety region.

6. A method as in claim 5, wherein the needle structure further comprises a plurality of tines which are advanceable from the needle in a distally diverging pattern, wherein the extent of advancement of the tines at least partly determines the size of the treatment region and/or the safety region.

7. A method as in claim 6, wherein the size of the projected boundary is adjusted by manually positioning a tine stop element on the probe.

8. A method as in claim 7, wherein tine stop element provides a physical limit on advancing the plurality of tines so that when the tines are advanced to the tine stop element the tines will be located in tissue within the treatment region and/or safety region.

9. A method as in claim 1, wherein deploying the needles comprises driving a servo motor controlled by the controller to advance the needle structure.

10. A method as in claim 6, wherein deploying the tines comprises driving a servo motor controlled by the controller to advance the tines.

11. A method as in claim 1, further comprising delivering energy through the needle structure to target tissue.

12. A method as in claim 11, further comprising controlling at least one of treatment power or treatment time to limit the extent of tissue treatment to within the treatment region and/or safety region.

13. A method as in claim 1, further comprising projecting virtual needle structure location information onto the display.

14. A method as in claim 13, wherein the virtual needle structure location information comprises markers representing locations on the needle.

15. A method as in claim 13, wherein the virtual needle location information is updated on the display as the probe stops are adjusted.

16. A method as in claim 1, further comprising projecting actual needle structure location information onto the display.

17. A method as in claim 16, wherein the actual needle structure location information is derived from sensors on the probe which track needle structure deployment.

18. A method as in claim 16, wherein the virtual needle location information is updated on the display as the needle structure is deployed.

19. A method as in claim 1, wherein adjusting the size and position of the projected boundary is performed while the probe is being held stationary.

* * * * *